(12) United States Patent
Malone et al.

(10) Patent No.: US 9,777,274 B2
(45) Date of Patent: Oct. 3, 2017

(54) **ANTISENSE MOLECULES FOR TREATMENT OF *STAPHYLOCOCCUS AUREUS* INFECTION**

(71) Applicant: Techulon Inc., Blacksburg, VA (US)

(72) Inventors: Brett Malone, Pearisburg, VA (US); Joshua Bryson, Blacksburg, VA (US)

(73) Assignee: TECHULON INC., Blacksburg, VA (US)

( * ) Notice: Subject to any disclaimer, the term of this patent is extended or adjusted under 35 U.S.C. 154(b) by 0 days.

(21) Appl. No.: 14/777,011

(22) PCT Filed: Mar. 14, 2014

(86) PCT No.: PCT/US2014/028855
§ 371 (c)(1),
(2) Date: Sep. 15, 2015

(87) PCT Pub. No.: WO2014/144442
PCT Pub. Date: Sep. 18, 2014

(65) Prior Publication Data
US 2016/0177309 A1    Jun. 23, 2016

Related U.S. Application Data

(60) Provisional application No. 61/786,946, filed on Mar. 15, 2013.

(51) Int. Cl.
| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *C08G 81/00* | (2006.01) | |
| *C12N 5/00* | (2006.01) | |

(52) U.S. Cl.
CPC .......... *C12N 15/1131* (2013.01); *C08G 81/00* (2013.01); *C12N 15/113* (2013.01); *C12N 2310/111* (2013.01); *C12N 2310/3181* (2013.01); *C12N 2310/351* (2013.01); *C12N 2310/3513* (2013.01)

(58) Field of Classification Search
None
See application file for complete search history.

(56) References Cited

U.S. PATENT DOCUMENTS

| | | |
|---|---|---|
| 5,116,195 A | 5/1992 | Pattarozzi |
| 5,521,291 A | 5/1996 | Curiel et al. |
| 5,527,675 A | 6/1996 | Coull et al. |
| 5,539,082 A | 7/1996 | Nielsen et al. |
| 5,623,049 A | 4/1997 | Loebberding et al. |
| 5,652,211 A | 7/1997 | Porro |
| 5,714,331 A | 2/1998 | Buchardt et al. |
| 5,736,336 A | 4/1998 | Buchardt et al. |
| 5,773,571 A | 6/1998 | Nielsen et al. |
| 5,786,461 A | 7/1998 | Buchardt et al. |
| 5,811,232 A | 9/1998 | Crooke et al. |
| 5,837,459 A | 11/1998 | Berg et al. |
| 5,874,564 A | 2/1999 | Ecker et al. |
| 5,891,625 A | 4/1999 | Buchardt et al. |
| 5,972,610 A | 10/1999 | Buchardt et al. |
| 5,986,053 A | 11/1999 | Ecker et al. |
| 6,107,470 A | 8/2000 | Nielsen et al. |
| 6,174,870 B1 | 1/2001 | Crooke et al. |
| 6,339,174 B1 | 1/2002 | Bogdanovic |
| 6,566,062 B1 | 5/2003 | Strauss et al. |
| 6,593,114 B1 | 7/2003 | Kunsch et al. |
| 6,703,492 B1 | 3/2004 | Kimmerly |
| 6,713,602 B1 | 3/2004 | Buchardt et al. |
| 6,737,248 B2 | 5/2004 | Kunsch et al. |
| 7,098,192 B2 | 8/2006 | Karras |
| 7,696,345 B2 | 4/2010 | Allerson et al. |
| 7,875,733 B2 | 1/2011 | Bhat et al. |
| 7,879,813 B2 | 2/2011 | Chatterton |
| 7,919,612 B2 | 4/2011 | Baker et al. |
| 7,939,677 B2 | 5/2011 | Bhat et al. |
| 7,943,581 B2 | 5/2011 | Divita et al. |
| 8,039,587 B2 | 10/2011 | Khan |
| 8,044,019 B2 | 10/2011 | Uno et al. |

(Continued)

FOREIGN PATENT DOCUMENTS

| | | |
|---|---|---|
| WO | WO 01/49775 A2 | 7/2001 |
| WO | WO 2007/009094 A2 | 1/2007 |

(Continued)

OTHER PUBLICATIONS

Altschul, S.F., "Amino Acid Substitution Matrices from an Information Theoretic Perspective," *Journal of Molecular Biology* 219(3):555-565, Elsevier, England (1991).
Berge, S.M., et al., "Pharmaceutical Salts," *Journal of Pharmaceutical Sciences* 66(1):1-19, Wiley, United States (1977).
Dirksen, A., et al., "Nucleophilic Catalysis of Hydrazone Formation and Transimination: Implications for Dynamic Covalent Chemistry," *Journal of the American Chemical Society* 128(49):15602-15603, American Chemical Society, United States (2006).
Fernandez-Lopez, S., et al., "Antibacterial Agents Based on the Cyclic D,L-α-peptide Architecture," *Nature* 412:452-455 (2001).
Haste, N.M., et al., "Activity of the Streptogramin Antibiotic Etamycin Against Methicillin-resistant *Staphylococcus aureus*," *The Journal of Antibiotics* 63(5):219-224, Nature Publishing Group, Japan (2010).

(Continued)

*Primary Examiner* — Sean McGarry
(74) *Attorney, Agent, or Firm* — Sterne, Kessler, Goldstein & Fox P.L.L.C.

(57) ABSTRACT

Disclosed are antisense molecules and compositions for the treatment of *Staphylococcus aureus* infection. The antisense molecules and compositions comprise nucleic acid molecules, such as RNA, DNA, or nucleic acid molecules with modified backbones, such as PNA. The antisense molecules and compositions inhibit expression of membrane stability proteins in *Staphylococcus aureus*; are optionally conjugated to cell penetration molecules such as peptides; and are optionally administered in the form of a nanoparticle composition.

16 Claims, 8 Drawing Sheets

(56) References Cited

U.S. PATENT DOCUMENTS

| | | | |
|---|---|---|---|
| 8,110,198 | B2 | 2/2012 | Stamm-Doucette et al. |
| 8,124,745 | B2 | 2/2012 | Allerson et al. |
| 8,138,383 | B2 | 3/2012 | Wakefield et al. |
| 8,207,293 | B2 | 6/2012 | Ronjat et al. |
| 8,211,468 | B2 | 7/2012 | Rozema et al. |
| 8,242,081 | B2 | 8/2012 | Divita et al. |
| 8,299,236 | B2 | 10/2012 | Chen et al. |
| 8,313,778 | B2 | 11/2012 | Seiler et al. |
| 8,314,229 | B2 | 11/2012 | Khvorova et al. |
| 8,338,366 | B2 | 12/2012 | Lin et al. |
| 8,354,093 | B2 | 1/2013 | Becker et al. |
| 8,354,387 | B2 | 1/2013 | Divita et al. |
| 8,357,664 | B2 | 1/2013 | Stein et al. |
| 8,372,969 | B2 | 2/2013 | Ying et al. |
| 8,377,898 | B2 | 2/2013 | Kandimalla et al. |
| 2004/0072743 | A1* | 4/2004 | Christensen ..... A61K 47/48238 514/44 R |
| 2005/0026189 | A1 | 2/2005 | Wang et al. |
| 2005/0192237 | A1 | 9/2005 | Iversen |
| 2009/0105115 | A1 | 4/2009 | Reineke |
| 2009/0124534 | A1 | 5/2009 | Reineke |

FOREIGN PATENT DOCUMENTS

| | | | |
|---|---|---|---|
| WO | WO-2012174543 | A2 | 12/2012 |
| WO | WO-2014144423 | A2 | 9/2014 |
| WO | WO-2014197091 | A2 | 12/2014 |

OTHER PUBLICATIONS

Hemp, S.T., et al., "Phosphonium-Containing Diblock Copolymers for Enhanced Colloidal Stability and Efficient Nucleic Acid Delivery," *Biomacromolecules* 13(8):2439-2445, American Chemical Society, United States (2012).

Henikoff, S. and Henikoff, J.G., "Amino Acid Substitution Matrices from Protein Blocks," *Proceedings of the National Academy of Sciences USA* 89(22):10915-10919, National Academy of Sciences, United States (1992).

Koshkin, A.A., et al., "LNA (Locked Nucleic Acids): Synthesis of the Adenine, Cytosine, Guanine, 5-methylcytosine, Thymine and Uracil Bicyclonucleoside Monomers, Oligomerisation and Unprecedented Nucleic Acid Recognition," *Tetrahedron* 54:3607-3630 (1998).

Nekhotiaeva, N., et al., "Cell Entry and Antimicrobial Properties of Eukaryotic Cell-penetrating Peptides," *FASEB Journal* 18(2):394-396, The Federation, United States (2004).

Nekhotiaeva, N., et al., "Inhibition of *Staphylococcus aureus* Gene Expression and Growth Using Antisense Peptide Nucleic Acids," *Molecular Therapy* 10(4):652-659, Academic Press, United States (2004).

Tachi, T., et al., "Position-dependent Hydrophobicity of the Antimicrobial Magainin Peptide Affects the Mode of Peptide-lipid Interactions and Selective Toxicity," *Biochemistry* 41(34):10723-10731, American Chemical Society, United States (2002).

Thompson, J.D., et al., "Clustal W: Improving the Sensitivity of Progressive Multiple Sequence Alignment Through Sequence Weighting, Position-specific Gap Penalties and Weight Matrix Choice," *Nucleic Acids Research* 22(22):4673-4680, Oxford University Press, England (1994).

Tranter, M., et al., "In Vivo Delivery of Nucleic Acids via Glycopolymer Vehicles Affords Therapeutic Infarct Size Reduction in Vivo," *Molecular Therapy* 20(3):601-608, Academic Press, United States (2012).

Wagner, E., et al., "A Simple Procedure for the Preparation of Protected 2'-O-methyl or 2'-O-ethyl Ribonucleoside-3'-O-phosphoramidites," *Nucleic Acids Research* 19(21):5965-5971, Oxford University Press, England (1991).

Wikler, M., et al., "Methods for Dilution Antimicrobial Susceptibility Tests for Bacteria that Grow Aerobically; Approved Standard—Seventh Edition," *Clinical and Laboratory Standards Institute* 26(2):M7-A7, Clinical and Laboratory Standards Institute, United States (2006).

Wongrakpanich, A., et al., "Poly(galactaramidoamine) is an Efficient Cationic Polymeric Non-viral Vector with Low Cytotoxicity for Transfecting Human Embryonic Kidney (HEK293) and Murine Macrophage (RAW264.7) Cells," *Pharmaceutical Development and Technology* 18(5):1255-1258, Informa Healthcare, England (2012).

International Search Report and Written Opinion, International Application No. PCT/US2014/028855, dated Sep. 26, 2014.

Co-pending U.S. Appl. No. 14/777,002, inventor Malone, B., I.A., filed Mar. 14, 2014.

Co-pending U.S. Appl. No. 14/777,007, inventor Malone, B., I.A., filed Mar. 14, 2014.

Hatamoto, M., et al., "Peptide nucleic acids (PNAs) antisense effect to bacterial growth and their application potentiality in biotechnology," *Appl. Microbiol. Biotechnol.* 86(2):397-402 (2010), Springer International Publishing AG (Cham, Switzerland).

\* cited by examiner

| Group # | N | Agent | Dose level (mg/kg) | Volume | Route of Admin. | Dosing Schedule | Terminal bleed (for serum) times | Tissue harvest |
|---|---|---|---|---|---|---|---|---|
| 1 | 15 | Vehicle (PBS) | N/A | 0.2 ml | IV | qd x 1 | 3 mice/group:<br>* 15 min.<br>* 30 min.<br>* 1 hr.<br>* 4 hr.<br>* 12 hr. | Harvest liver, kidney, lung, and spleen; snap freeze and store at -80°C |
| 2 | 15 | Anti-PBP1 PNA-peptide | 1 | 0.2 ml | IV | qd x 1 | | |
| 3 | 15 | Anti-PBP1 PNA-peptide | 3.3 | 0.2 ml | IV | qd x 1 | | |
| 4 | 15 | Anti-PBP1 PNA-peptide | 10 | 0.2 ml | IV | qd x 1 | | |

Terminally bleed 3 mice/group/time point at 15 min, 30 min, 1 hr, 4 hr, and 12 hr.

FIGURE 4

| Group # | N | Agent | Dose level (mg/kg) | Volume | Route of Admin. | Dosing Schedule |
|---|---|---|---|---|---|---|
| 1 | 10 | Vehicle (PBS) | N/A | 0.2 ml | IV | qd x 7 |
| 2 | 10 | Anti-PBP1 PNA-peptide | 10 | 0.2 ml | IV | qd x 7 |
| 3 | 10 | Anti-PBP1 PNA-peptide | 10 | 0.2 ml | IV | q2d x 4 |
| 4 | 10 | Anti-PBP1 PNA-peptide | 10 | 0.2 ml | IV | q3d x 3 |

SEQUENCE LISTING

```
<160> NUMBER OF SEQ ID NOS: 44

<210> SEQ ID NO 1
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 1
cgtcatacgc ggtcc                                                      15

<210> SEQ ID NO 2
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 2
atccatcgta aatcc                                                      15

<210> SEQ ID NO 3
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 3
cattactacg ca                                                         12

<210> SEQ ID NO 4
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 4
tttcgtcatt aa                                                         12

<210> SEQ ID NO 5
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 5
tcatacgcgg tc                                                         12
```

<210> SEQ ID NO 6
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 6
ccgacatatt ac                                                          12

<210> SEQ ID NO 7
<211> LENGTH: 12
<212> TYPE: DNA
<213> ORGANISM: Artificial Sequence
<220> FEATURE:
<223> OTHER INFORMATION: synthetic antisense strand

<400> SEQUENCE: 7
catcgtaaat cc                                                          12

<210> SEQ ID NO 8
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 8
tgcatccaaa ctgaa                                                       15

<210> SEQ ID NO 9
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 9
attcatattc ggtca                                                       15

<210> SEQ ID NO 10
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 10
acaaaaatca taact                                                       15

<210> SEQ ID NO 11
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 11
ttaaacatgg tcttt                                                       15

<210> SEQ ID NO 12
<211> LENGTH: 15
<212> TYPE: DNA
<213> ORGANISM: Artificial Sequence
<220> FEATURE:
<223> OTHER INFORMATION: synthetic antisense strand

```
<400> SEQUENCE: 12
tactcatttt atcaa                                                  15

<210> SEQ ID NO 13
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 13
gattttcgtc attaa                                                  15

<210> SEQ ID NO 14
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 14
agtgtgtcat tatat                                                  15

<210> SEQ ID NO 15
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 15
gtctcatgtg tttcc                                                  15

<210> SEQ ID NO 16
<211> LENGTH: 15
<212> TYPE: DNA
<213> ORGANISM: Artificial Sequence
<220> FEATURE:
<223> OTHER INFORMATION: synthetic antisense strand

<400> SEQUENCE: 16
tgtcatttcg ttttc                                                  15

<210> SEQ ID NO 17
<211> LENGTH: 10
<212> TYPE: PRT
<213> ORGANISM: Artificial Sequence
<220> FEATURE:
<223> OTHER INFORMATION: KKF peptide

<400> SEQUENCE: 17

Lys Phe Phe Lys Phe Phe Lys Phe Phe Lys
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: RFF peptide

<400> SEQUENCE: 18

Arg Phe Phe Arg Phe Phe Arg Phe Phe Arg
 1               5                  10
```

<210> SEQ ID NO 19
<211> LENGTH: 23
<212> TYPE: PRT
<213> ORGANISM: Artificial Sequence
<220> FEATURE:
<223> OTHER INFORMATION: Magainin 2

<400> SEQUENCE: 19

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 20
<211> LENGTH: 21
<212> TYPE: PRT
<213> ORGANISM: Artificial Sequence
<220> FEATURE:
<223> OTHER INFORMATION: Transportin 10

<400> SEQUENCE: 20

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 21
<211> LENGTH: 6
<212> TYPE: PRT
<213> ORGANISM: Artificial Sequence
<220> FEATURE:
<223> OTHER INFORMATION: cyclic d,l-alpha-peptide

<400> SEQUENCE: 21

Lys Lys Leu Trp Leu Trp
1               5

<210> SEQ ID NO 22
<211> LENGTH: 8
<212> TYPE: PRT
<213> ORGANISM: Artificial Sequence
<220> FEATURE:
<223> OTHER INFORMATION: cyclic d,l-alpha-peptide

<400> SEQUENCE: 22

Arg Arg Lys Trp Leu Trp Leu Trp
1               5

<210> SEQ ID NO 23
<211> LENGTH: 8
<212> TYPE: PRT
<213> ORGANISM: Artificial Sequence
<220> FEATURE:
<223> OTHER INFORMATION: cyclic d,l-alpha-peptide

<400> SEQUENCE: 23

Lys Gln Arg Trp Leu Trp Leu Trp
1               5

<210> SEQ ID NO 24
<211> LENGTH: 18
<212> TYPE: PRT
<213> ORGANISM: Artificial Sequence
<220> FEATURE:
<223> OTHER INFORMATION: amphipathic peptide

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
<211> LENGTH: 16
<212> TYPE: PRT
<213> ORGANISM: Artificial Sequence
<220> FEATURE:
<223> OTHER INFORMATION: PENETRATIN 1 peptide

<400> SEQUENCE: 25

Arg Gln Ile Lys Ile Trp Phe Gln Asn Arg Arg Met Lys Trp Lys Lys
1               5                   10                  15

<210> SEQ ID NO 26
<211> LENGTH: 12
<212> TYPE: PRT
<213> ORGANISM: Artificial Sequence
<220> FEATURE:
<223> OTHER INFORMATION: TAT peptide

<400> SEQUENCE: 26

Gly Arg Lys Lys Arg Arg Gln Arg Arg Arg Pro Gln
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Indolicidin peptide

<400> SEQUENCE: 27

Ile Leu Pro Trp Lys Trp Pro Trp Trp Pro Trp Arg Arg
1               5                   10

<210> SEQ ID NO 28
<211> LENGTH: 15
<212> TYPE: DNA
<213> ORGANISM: Artificial Sequence
<220> FEATURE:
<223> OTHER INFORMATION: t-RNA-dependent lipid II-Gly-glycine ligase
      (FmhB)

<400> SEQUENCE: 28
ttttccatga tttat                                                15

<210> SEQ ID NO 29
<211> LENGTH: 15
<212> TYPE: DNA
<213> ORGANISM: Artificial Sequence
<220> FEATURE:
<223> OTHER INFORMATION: noncoding synthetic strand

<400> SEQUENCE: 29
aacattttgg ttttt                                                15

<210> SEQ ID NO 30
<211> LENGTH: 12
<212> TYPE: DNA
<213> ORGANISM: Artificial Sequence
<220> FEATURE:
<223> OTHER INFORMATION: control synthetic strand

```
<400> SEQUENCE: 30
tccatgattt at                                                             12

<210> SEQ ID NO 31
<211> LENGTH: 1149
<212> TYPE: DNA
<213> ORGANISM: Staphylococcus aureus

<400> SEQUENCE: 31
atgtcggata aatattatag atctgcgtat atgaatgtag atttaaacgc tgttgcatca           60
aatttcaaag tattcagtac attgcatcca aataaaacag tgatggctgt cgttaaagcc          120
aatgcctatg gactaggtag tgttaaagta gcacgtcatt aatggaaaa tggcgccaca          180 ttttttgctg tagcaacgtt agatgaagcg atagaactta gaatgcatgg gattactgct          240
aaaattttag tcttaggtgt gttaccagct aaagatattg ataaagcgat acaacaccga          300
gttgccttaa cggttccgtc taaacagtgg ttgaaagaag caattaaaaa catttctggt          360
gagcaagaga aaaagttatg gttgcacatt aaattagata caggaatggg acgtttaggt          420
attaaagata ctaaaacgta tcaagaagtg attgaaatca ttcaacaata tgagcaactt          480
gtatttgaag gcgtgtttac acactttgcc tgtgctgacg aaccaggaga tatgacaact          540
gaacaatatc aacgttttaa agatatggtc aatgaagcaa ttaaacctga atatatacat          600
tgtcagaact cagcaggctc tctattaatg gattgccaat tctgtaatgc aataagacca          660
ggaatttccc tttatggata ttatccatca gagtatgtac agcaaaaagt taaagtacac          720
cttaaaccaa gtgtgcaatt aattgctaat gtagttcaaa caaagacgct acaagcgggt          780
gagtctgtaa gttatggtgc aacttataca gctactgacc caactacaat agcattgtta          840
cctattggat atgcagatgg ctatttacgc ataatgcaag gtagctttgt aaatgtaaat          900
ggtcatcaat gcgaagttat tggtcgcgta tgtatggatc agacaattgt taaagtgcca          960
gatcaagtta agctggaga ttcggtgatt taatagata atcatagaga aagtccacag          1020
tcggtagagg tggtagctga aaagcaacat actattaatt atgaagtgct ttgtaacttg          1080
tcgagacgtt tgccgcgaat ctatcatgat ggtgatcaac gttttgtaac aaatgaattg          1140
ttaaaataa                                                               1149

<210> SEQ ID NO 32
<211> LENGTH: 2076
<212> TYPE: DNA
<213> ORGANISM: Staphylococcus aureus

<400> SEQUENCE: 32
ttgttaaaaa gactaaaaga aaatcaaat gatgaaatcg ttcaaaatac aattaacaag            60
agaattaact ttatatttgg tgtgattgta tttatttttg cagtactagt actacgttta          120
ggttatttac aaatcgcaca aggctcacat tataaacaaa ttataaaaaa tgatgaaaac          180
attacagtaa atgagtctgt gccaagaggt cgtattttag acagaatgg gaaagttta          240 gttgataatg cttctaaaat ggctattaca tatactaggg gtcgaaaaac aacacaatcg          300
gaaatgttgg atacggctga aaagttatca aagctaatca agatggatac taagaagatt          360
acagaacgtg ataagaaaga tttctggatt cagttgcatc ctaaaaaagc aaaagcaatg          420
atgacaaaag aacaagctat gttagcagat ggaagtatta acaagatca atatgataaa          480 caactgttat cgaaaatcgg aaaatcacaa ttagatgaat tgtcttctaa agatttacaa          540
gttttagcca ttttttcgaga gatgaatgca ggaacagttt tagatccaca aatgataaaa          600
```

```
aatgaagatg tcagtgaaaa agagtatgca gcagtttctc agcaactttc caaattacca      660
ggtgttaaca cgtctatgga ttgggataga aaatatccat atggcgacac tttaagaggt      720
atatttggag atgtatcgac acctgctgaa ggtattccaa aagaattgac agaacattac      780
ttatccaaag gatattcacg caatgatcgt gttggaaaat cttacctaga atatcaatat      840
gaagatgtat tgcgtggtaa gaagaaagaa atgaaataca acggacaa atctggaaaa       900 gttacatctt cagaagtgtt aaatcctggc gctcgcggtc aagatttgaa attaacaatc      960
gatatagatc ttcaaaaaga agtagaatca ttattagata acaaattaa gaagcttcgc      1020 agccaaggtg ccaaagatat ggataatgct atgatggttg tacaaaatcc taaaaatgga      1080
gacattcttg cgcttgccgg aaagcagatt aataagagtg gtaaaatgac tgattatgac      1140
attggtacgt ttacttctca atttgcggtt ggatcttctg taaaaggtgg aacattatta      1200
gctggttatc agaataaagc tatcaaagtt ggagaaacaa tggtcgatga accattacat      1260
ttccaaggtg gttgacaaa acgatcatac tttaataaaa acgggcatgt atctattaat       1320
gataagcaag ctttgatgca ttcatcaaac gtatatatgt ttaaaacagc attaaaatta      1380
gcgggagacc cttattattc tggtatggct ttaccttcag acataagttc acctgcccaa      1440
aagctaagaa gaggattaaa tcaagtaggt ttaggtgtga aaacaggaat agatttacca      1500
aatgaaacaa gaggtcaaat cgaaccatta acaaataatc caggtaatta tctagattta      1560
tcaattggtc aatatgatac ctatacacca ttacaattat cacaatatgt ttcaactata      1620
gcgaatgatg ttatagaat acagccacac attggattaa cgattcatga atcaactaat      1680
aaagatgagg ttggtccact caagaagaaa attaatggca ccgtattgaa caaggttaat      1740
aatactgaaa aagaaatcaa acaaattcaa gaaggattca aaatggcatt taatgataaa      1800
gatggtactg gatatgttag ttttaaagat acagtagtcc ctactgctgg taaaacgggt      1860
accgctgaag tgttccaaaa cggagagcca agagttaact ctacttatat aggatacgcg      1920
ccaattgatg atccaaaatt agcgttttca attgtatata caaatcagcc tgtaccacca      1980
ccatggttaa caggtggaga cttaggtaga gatgtaatta actactactt taagcagtta      2040
ggtaaagatg ataaaaataa agacaaagac aaataa                               2076

<210> SEQ ID NO 33
<211> LENGTH: 1071
<212> TYPE: DNA
<213> ORGANISM: Staphylococcus aureus

<400> SEQUENCE: 33
atgacaaaag aaaatatttg tatcgttttt ggagggaaaa gtgcagaaca cgaagtatcg       60
attctgacag cacaaaatgt attaaatgca atagataaag acaaatatca tgttgatatc      120
atttatatta ccaatgatgg tgattggaga agcaaaata atattacagc tgaaattaaa      180
tctactgatg agcttcattt agaaaatgga gaggcgcttg agatttcaca gctattgaaa      240
gaaagtagtt caggacaacc atacgatgca gtattcccat tattacatgg tcctaatggt      300
gaagatggca cgattcaagg gcttttttgaa gttttggatg taccatatgt aggaaatggt      360
gtattgtcag ctgcaagttc tatggacaaa cttgtaatga acaattatt tgaacatcga      420 gggttaccac agttacctta tattagtttc ttacgttctg aatatgaaaa atatgaacat      480 aacatttta aattagtaaa tgataaatta aattacccag tctttgttaa acctgctaac      540
ttagggtcaa gtgtaggtat cagtaaatgt aataatgaag cggaacttaa agaaggtatt      600
```

| aaagaagcat tccaatttga ccgtaagctt gttatagaac aaggcgttaa cgcacgtgaa | 660 |
| attgaagtag cagttttagg aaatgactat cctgaagcga catggccagg tgaagtcgta | 720 |
| aaagatgtcg cgttttacga ttacaaatca aaatataaag atggtaaggt tcaattacaa | 780 |
| attccagctg acttagacga agatgttcaa ttaacgctta gaaatatggc attagaggca | 840 |
| ttcaaagcga cagattgttc tggtttagtc cgtgctgatt tctttgtaac agaagacaac | 900 |
| caaatatata ttaatgaaac aaatgcaatg cctggattta cggctttcag tatgtatcca | 960 |
| aagttatggg aaaatatggg cttatcttat ccagaattga ttacaaaact tatcgagctt | 1020 |
| gctaaagaac gtcaccagga taaacagaaa aataaataca aaattgacta a | 1071 |

<210> SEQ ID NO 34
<211> LENGTH: 801
<212> TYPE: DNA
<213> ORGANISM: Staphylococcus aureus

<400> SEQUENCE: 34

| atgaataaac caataggtgt aatagactct ggtgtcggag gtttgacagt agctaaagaa | 60 |
| attatgcgtc agttgccaaa tgagacgatt tattacttag gtgatattgg acgatgtcca | 120 |
| tatgggccaa gaccaggaga acaagtaaaa caatatacag ttgaaatcgc tcgtaaatta | 180 |
| atggaatttg atataaaaat gctcgtgatt gcttgtaata cagcaactgc tgtagcttta | 240 |
| gaatatttac aaaagacctt atcaatccca gtgattggtg taattgaacc aggtgctaga | 300 |
| acagcaataa tgactactag aaatcaaaat gtattagtac taggaactga aggcacaatt | 360 |
| aaatctgaag catatcgtac gcatattaaa cgtatcaatc cacatgtaga ggtacatggc | 420 |
| gttgcctgtc caggttttgt gccacttgta gaacaaatga gatatagtga tccaacaatt | 480 |
| acaagcattg tcattcatca aacactgaaa cgttggcgta atagtgagtc tgatactgtc | 540 |
| attttaggat gtacccacta tccattgctc tataaaccta tctatgatta ttttggtggt | 600 |
| aaaaagacag tgatttcgtc tggattagaa acggctcgtg aagttagtgc attgctaaca | 660 |
| tttagtaatg aacatgcaag ttatactgaa catccagatc atcgattttt tgcaacaggt | 720 |
| gatcctactc acattactaa cattatcaaa gagtggttaa atttatctgt caatgtggaa | 780 |
| cgtatatcag tgaatgacta g | 801 |

<210> SEQ ID NO 35
<211> LENGTH: 2235
<212> TYPE: DNA
<213> ORGANISM: Staphylococcus aureus

<400> SEQUENCE: 35

| atggcgaagc aaaaaattaa aattaaaaaa aataaaatag ggcagtcct acttgttggt | 60 |
| ttattcggac tgctcttttt tatattggtt ttaagaattt catatatcat gattactgga | 120 |
| cattctaatg gtcaagattt agtcatgaag gcaaatgaaa agtatttagt taagaatgca | 180 |
| caacaaccag aacgaggaaa gatatatgat cgtaatggta agtgctagc agaagatgta | 240 |
| gaaagatata aacttgttgc agtaatagat aaaaaggcga gtgccaattc taaaaaacct | 300 |
| aggcatgtag ttgataaaaa agagactgca aagaaattat ctacagtcat taatatgaag | 360 |
| ccagaggaaa ttgaaaagag acttagtcaa aagaaagctt ccaaattga atttggacgc | 420 |
| aaaggaacaa atttaacgta tcaggacaaa ttgaaaatag agaaaatgaa tttgcctggt | 480 |
| atttctttat tgcctgaaac agaacgcttt tatccaaatg gcaattttgc atcacactta | 540 |
| attggtagag ctcagaaaaa tccggatact ggtgaactta aaggtgcact tggagttgaa | 600 |

| | |
|---|---|
| aagattttg atagttattt aagtggatct aaaggatcat tgagatatat tcatgatatt | 660 |
| tggggatata tcgcaccaaa tactaaaaaa gagaagcagc ctaaacgtgg tgatgatgtc | 720 |
| catttaacaa tcgattcaaa tattcaagta tttgttgaag aagctttaga tggcatggtt | 780 |
| gaaagatacc agccgaaaga tttatttgcg gttgtcatgg atgccaaaac tggagaaatt | 840 |
| ttagcataca gtcagcgacc aacatttaat cctgaaactg gtaaagactt tggtaaaaag | 900 |
| tgggcaaatg accttatca aaacacatac gagcctggat caacatttaa atcatatggg | 960 |
| ttagcagctg ctattcaaga aggtgctttt gatcctgata agaaatataa atctggacat | 1020 |
| agagatatta tggttcacg tatttcagac tggaatagga tcggttgggg tgaaatccca | 1080 |
| atgtcactcg gatttactta ttcatctaat acattgatga tgcatttaca agatttagtt | 1140 |
| ggtgcagaca aaatgaaatc ttggtatgaa cgatttggat ttggaaaatc aactaaaggt | 1200 |
| atgtttgatg gagaagcacc tggtcaaatt ggatggagta atgagttgca acaaaaaacg | 1260 |
| tcatcatttg gtcaatcgac aacagtaaca cctgttcaaa tgttacaagc gcaatcagcg | 1320 |
| ttctttaatg atggtaatat gttaaaacca tggtttgtga atagcgttga aaatcctgtt | 1380 |
| agtaaaagac aattttataa agggcaaaaa caaatcgcag gcaaaccaat aacaaaagat | 1440 |
| actgctgaaa aagttgaaaa gcaattggat ttagttgtga atagtaagaa gagtcacgct | 1500 |
| gcaaactatc gtattgatgg ttatgaggtc gaaggtaaga ctggtacagc acaagtcgct | 1560 |
| gcacctaatg gtggtggata cgttaaaggt ccaaacccat attttgtaag ttttatgggt | 1620 |
| gacgcgccga agaaaaatcc taaagttatt gtatacgctg gtatgagctt ggcacaaaaa | 1680 |
| aatgaccaag aagcttatga attaggtgtt agtaaagcgt taaaccaat aatggaaaat | 1740 |
| actttgaaat atttaaatgt aggtaaatca aagatgaca catctaatgc agagtatagt | 1800 |
| aaagtgccag atgttgaagg tcaagacaaa caaaaagcta ttgataatgt gagtgcaaaa | 1860 |
| tcattagaac cagttactat tggttctggc acacaaataa aagcacaatc tataaaagca | 1920 |
| gggaataaag tcttacctca gtaaagta ctgttattaa cagatggaga cttaactatg | 1980 |
| cctgacatgt caggatggac gaaagaagat gtcattgctt ttgaaaacct aacaaatatt | 2040 |
| aaagtaaatt taaaggtag cggttttgtg tcccaccaat caattagtaa gggacaaaaa | 2100 |
| cttactgaaa aagataaaat agacgtagaa ttttcatcag agaatgtaga cagcaattcg | 2160 |
| acgaataatt ctgattcaaa ttcagatgat aagaagaaat ctgacagtaa aactgacaag | 2220 |
| gataagtcgg actaa | 2235 |

<210> SEQ ID NO 36
<211> LENGTH: 966
<212> TYPE: DNA
<213> ORGANISM: Staphylococcus aureus

<400> SEQUENCE: 36

| | |
|---|---|
| atgatttttg tatatgcgtt attagcgcta gtgattacat ttgttttggt acctgtttta | 60 |
| atacctacat taaaaaggat gaaatttggt caaagtattc gagaagaagg tccacaaagc | 120 |
| catatgaaga agactggtac accaacgatg ggtggactaa catttctatt aagtattgtg | 180 |
| ataacgtctt tggtggctat tatatttgta gatcaagcta atccaatcat actgttatta | 240 |
| tttgtgacga ttggttttgg gttaattggt tttatagatg attatattat tgttgttaaa | 300 |
| aagaataacc aaggtttaac aagtaaacag aagttttgg cgcaaattgg tattgcgatt | 360 |
| attttctttg ttttaagtaa tgtgttcat ttggtgaatt tttctacgag catacatatt | 420 |

-continued

```
ccatttacga atgtagcaat cccactatca tttgcatatg ttattttcat tgttttttgg    480
caagtaggtt tttctaatgc ggtaaattta acagatggtt tagatggatt agcaactgga    540
ctgtcaatta tcggatttac aatgtatgcc atcatgagct ttgtgttagg agaaacggca    600
attggtattt tctgtatcat tatgttgttt gcacttttag gattttttacc atataacatt    660 aaccctgcta aagtgtttat gggagataca ggtagcttag ctttaggtgg tatatttgct    720
acgatttcaa tcatgcttaa tcaggaatta tcattaattt ttataggttt agtattcgta    780
attgaaacat tatctgttat gttacaagtc gctagcttta aattgactgg aaagcgtata    840
tttaaaatga gtccgattca tcatcatttt gaattgatag gatggagcga atggaaagta    900
gttacagtat tttgggctgt tggtctgatt tcaggtttaa tcggtttatg gattggagtg    960
cattaa                                                                966
```

<210> SEQ ID NO 37
<211> LENGTH: 1314
<212> TYPE: DNA
<213> ORGANISM: Staphylococcus aureus

<400> SEQUENCE: 37

```
atgagacagt ggacggcaat ccatctagcg aaattggcgc gtaaagcaag tagagcagta     60
ggtaaaagag gaacagattt acctggacaa atcgctagaa aagtggatac agatatatta    120
agaaaattag cagagcaagt tgatgatatt gtatttatca gtggaacaaa tggtaaaaca    180
acgacttcaa acttaattgg acatacttta aaagcaaata atattcaaat tatacacaat    240
aatgaaggtg ctaatatggc tgcaggtata acttttgcat tcatcatgca atcaacacct    300
aagactaaaa ttgcggtaat cgaaattgat gaaggttcga ttccacgtgt gttaaaagaa    360
gttacacctt caatgatggt atttactaat ttctttagag atcaaatgga tcgcttcggt    420
gaaattgata ttatggttaa taacattgca gagacaatta gtaataaagg catcaaatta    480
ttgctaaatg ctgatgatcc atttgtgagt cgtttgaaaa tcgcaagtga tacgattgtg    540
tactatggta tgaaagcaca tgcccatgaa tttgaacaaa gtacgatgaa tgaaagtaga    600
tattgtccaa actgtggtcg cttattgcaa tacgattata ttcattataa tcaaattggt    660
cattatcact gtcagtgtgg tttcaaacga gagcaagcaa aatatgaaat atcaagttt t    720 gatgtggcac cgttttata tttaaatatc aatgatgaaa aatatgatat gaaaattgca    780
ggtgacttta acgcttataa cgcgttagca gcatatactg ttttaagaga gctagggtta    840
aatgaacaaa caattaaaaa tggctttgaa acgtatacat cagacaatgg tcgtatgcag    900
tactttaaaa aagaacgaaa agaagcgatg atcaatttag ctaaaaatcc tgcaggaatg    960
aatgcaagtt tatcagttgg tgaacaatta gaaggcgaaa aagtgtatgt tatttcgcta    1020
aatgataacg ctgcagatgg tcgagatact tcatggattt atgatgcaga tttttgaaaaa    1080 ttatctaagc aacaaattga agctatcatc gtgacaggta cacgagcaga agaacttcaa    1140
ttgcgattga agttagcaga ggttgaagta ccaattatag ttgagcgtga tatttataaa    1200
gcaacggcaa agactatgga ttataaaggt ttcacagttg caataccaaa ctatacatca    1260
ttagcgccta tgcttgaaca attaaaccgt tcgtttgaag gaggtcaatc ataa           1314
```

<210> SEQ ID NO 38
<211> LENGTH: 1266
<212> TYPE: DNA
<213> ORGANISM: Staphylococcus aureus

<400> SEQUENCE: 38

-continued

```
atggaaaaga tgcatatcac taatcaggaa catgacgcat tgttaaatc ccacccaaat      60 ggagatttat tacaattaac gaaatgggca gaaacaaaga aattaactgg atggtacgcg     120
cgaagaatcg ctgtaggtcg tgacggtgaa gttcagggtg ttgcgcagtt acttttaaa     180 aaagtaccta aattacctta tacgctatgt tatatttcgc gtggttttgt tgttgattat     240
agtaataaag aagcgttaaa tgcattgtta gacagtgcaa agaaattgc taaagctgag     300 aaagcgtatg caattaaaat cgatcctgat gttgaagttg ataaaggtac agatgctttg     360
caaaatttga agcgcttgg ttttaaacat aaaggattta agaaggttt atcaaaagac     420 tacatccaac cacgtatgac tatgattaca ccaattgata aaaatgatga tgagttatta     480
aatagttttg aacgccgaaa tcgttcaaaa gtgcgcttgg ctttaaagcg aggtacgaca     540
gtagaacgat ctgatagaga aggtttaaaa acatttgctg agttaatgaa atcactggg     600 gaacgcgatg gcttcttaac gcgtgatatt agttactttg aaaatattta tgatgcgttg     660
catgaagatg gagatgctga actatttta gtaaagttgg atccaaaaga aaatatagcg     720
aaagtaaatc aagaattgaa tgaacttcat gccgaaattg ctaaatggca gcagaagatg     780
aaaacatctg aaaagcaagc taaaaaagcg caaaatatga ttaatgatgc gcaaaataaa     840
attgctaaaa atgaagattt aaaacgagac ctagaagctt tagaaaagga acatcctgaa     900
ggtatttatc tttctggtgc actattaatg tttgctggct caaaatcata ttacttatat     960
ggtgcgtctt ctaatgaatt tagagatttt ttaccaaatc atcatatgca gtatacgatg    1020
atgaagtatg cacgtgaaca tggtgcaaca acttacgatt tcggtggtac agataatgat    1080
ccagataaag actcagaaca ttatggatta tgggcattta aaaaagtgtg gggaacatac    1140
ttaagtgaaa agattggtga atttgattat gtattgaatc agccattgta ccaattaatt    1200
gagcaagtta accgcgtttt aacaaaagct aaaattaaaa tatctcgtaa attaaaacga    1260
aaatag                                                               1266
```

<210> SEQ ID NO 39
<211> LENGTH: 1263
<212> TYPE: DNA
<213> ORGANISM: Staphylococcus aureus

<400> SEQUENCE: 39

```
atgaagttta caaatttaac agctaaagag tttggtgcct ttacagatag catgccatac      60
agtcatttca cgcaaactgt tggccactat gagttaaagc ttgctgaagg ttatgaaaca     120
catttagtgg gaataaaaaa caataataac gaggtcattg cagcttgctt acttactgct     180
gtacctgtta tgaaagtgtt caagtatttt tattcaaatc gcggtccagt gattgattat     240
gaaaatcaag aactcgtaca ctttttcttt aatgaattat caaatatgt taaaaaacat     300 cgttgtctat acctacatat cgatccatat ttaccatatc aatacttgaa tcatgatggc     360
gagattacag gtaatgctgg taatgattgg ttctttgata aatgagtaa cttaggattt     420 gaacatactg gattccataa aggatttgat cctgtgctac aaattcgtta tcactcagtg     480
ttagatttaa aagataaaac agcagatgac atcattaaaa atatggatgg acttagaaaa     540
agaaacacga aaaagttaa aagaatggt gttaaagtaa gattttatc tgaagaagaa     600 ctaccaattt ttagatcatt tatggaagat acgtcagaat caaaagcttt tgctgatcgt     660
gatgacaaat tttactacaa tcgcttaaaa tattacaaag accgtgtgtt agtaccttta     720
gcgtatatca actttgatga atatattaaa gaactaaacg aagagcgtga tattttaaat    780
```

| | |
|---|---|
| aaagatttaa ataaagcgtt aaaggatatt gaaaaacgtc ctgaaaataa aaaagcacat | 840 |
| aacaagcgag ataacttaca acaacaactt gatgcaaatg agcaaaagat tgaagaaggt | 900 |
| aaacgtctac aagaagaaca tggtaatgaa ttacctatct ctgctggttt cttctttatc | 960 |
| aatccatttg aagttgttta ttatgctggt ggtacatcaa atgcattccg tcattttgcc | 1020 |
| ggaagttatg cagtgcaatg ggaaatgatt aattatgcat taaatcatgg cattgaccgt | 1080 |
| tataatttct atggtgttag tggtaaattt acagaagatg ctgaagatgc tggtgtagtt | 1140 |
| aaattcaaaa aaggttacaa tgctgaaatt attgaatatg ttggtgactt tattaaacca | 1200 |
| attaataaac ctgtttacgc agcatatacc gcacttaaaa agttaaaga cagaattttt | 1260 |
| tag | 1263 |

<210> SEQ ID NO 40
<211> LENGTH: 1266
<212> TYPE: DNA
<213> ORGANISM: Staphylococcus aureus

<400> SEQUENCE: 40

| | |
|---|---|
| atggataaaa tagtaatcaa aggtggaaat aaattaacgg gtgaagttaa agtagaaggt | 60 |
| gctaaaaatg cagtattacc aatattgaca gcatctttat tagcttctga taaaccgagt | 120 |
| aaattagtta atgttccagc tttaagtgat gtagaaacaa taataatgt attaacaact | 180 |
| ttaaatgctg acgttacata caaaaaggac gaaaatgctg ttgtcgttga tgcaacaaag | 240 |
| actctaaatg aagaggcacc atatgaatat gttagtaaaa tgcgtgcaag tattttagtt | 300 |
| atgggacctc ttttagcaag actaggacat gctattgttg cattgcctgg tggttgtgca | 360 |
| attggaagta gaccgattga gcaacacatt aaaggttttg aagctttagg cgcagaaatt | 420 |
| catcttgaaa tggtaatat ttatgctaat gctaaagatg gattaaaagg tacatcaatt | 480 |
| catttagatt ttccaagtgt aggagcaaca caaaatatta ttatggcagc atcattagct | 540 |
| aagggtaaga ctttaattga aaatgcagct aaagaacctg aaattgtcga tttagcaaac | 600 |
| tacattaatg aaatgggtgg tagaattact ggtgctggta cagacacaat tacaatcaat | 660 |
| ggtgtagaat cattacatgg tgtagaacat gctatcattc cagatagaat tgaagcaggc | 720 |
| acattactaa tcgctggtgc tataacgcgt ggtgatattt ttgtacgtgg tgcaatcaaa | 780 |
| gaacatatgg cgagtttagt ctataaacta aagaaaatgg cgttgaatt ggactatcaa | 840 |
| gaagatggta ttcgtgtacg tgctgaaggg gaattacaac ctgtagacat caaaacacta | 900 |
| ccacatcctg gattcccgac tgatatgcaa tcacaaatga tggcattgtt attaacggca | 960 |
| aatggtcata aagtcgtaac cgaaactgtt tttgaaaacc gttttatgca tgttgcagag | 1020 |
| ttcaaacgta tgaatgctaa tatcaatgta gaaggtcgta gtgctaaact tgaaggtaaa | 1080 |
| agtcaattgc aaggtgcaca agttaaagcg actgatttaa gagcagcagc agccttaatt | 1140 |
| ttagctggat tagttgctga tggtaaaaca agcgttactg aattaacgca cctagataga | 1200 |
| ggctatgttg acttacacgg taaattgaag caattaggtg cagacattga acgtattaac | 1260 |
| gattaa | 1266 |

<210> SEQ ID NO 41
<211> LENGTH: 1071
<212> TYPE: DNA
<213> ORGANISM: Staphylococcus aureus

<400> SEQUENCE: 41

| | |
|---|---|
| atgacgaaaa tcgcatttac cggaggggga acagttggac acgtatcagt aaatttaagt | 60 |

-continued

```
ttaattccaa ctgcattatc acaaggttat gaagcgcttt atattggttc taaaaatggt      120
attgaaagag aaatgattga atcacaacta ccagaaatta gtattatcc tatttcgagt       180 ggtaaattaa gaagatatat ttctttagaa aatgccaaag acgtatttaa agtattgaaa      240
ggtattcttg atgctcgtaa agttttgaaa aagaaaaac ctgatctatt attttcaaaa       300
ggtggatttg tatctgtgcc tgttgttatt gcagccaaat cattaaatat accaactatt     360
attcatgaat ctgacttaac accaggatta gcgaataaga tagcacttaa atttgccaag     420
aaaatatata caacatttga agaaacgcta aactacttac ctaaagagaa agctgatttt     480
attggagcaa caattcgaga agatttaaaa aatggtaatg cacataatgg ttatcaatta     540
acaggcttta atgaaaataa aaaagtttta cttgttatgg gtggaagctt aggaagtaaa     600
aaattaaata gcattattcg cgaaaactta gatgcattat acaacaata tcaagtgata     660 catttaactg gtaaaggatt aaaagatgct caagttaaaa aatcaggata tatacaatat    720
gaatttgtta agaggattt aacagattta ttagcaatta cggatacagt aataagtaga    780
gctggatcaa atgcgattta tgagttctta acattacgta taccaatgtt attagtacca    840
ttaggtttag atcaatcccg aggcgaccaa attgacaatg caaatcattt tgctgataaa    900
ggttatgcta aaacgattga tgaagaacaa ttaacagcac aaattttatt acaagaacta    960
aatgaaatgg aacaggaaag aactcgaatt atcaataata tgaaatcgta tgaacaaagt   1020
tatacgaaag aagctttatt tgataagatg attaaagacg cattgaatta a           1071
```

<210> SEQ ID NO 42
<211> LENGTH: 1314
<212> TYPE: DNA
<213> ORGANISM: Staphylococcus aureus

<400> SEQUENCE: 42

```
atgacacact atcattttgt cggaattaaa ggttctggca tgagttcatt agcacaaatc       60
atgcatgatt taggacatga agttcaagga tcggatattg agaactacgt atttacagaa      120
gttgctctta gaaataaggg gataaaata ttaccatttg atgctaataa cataaaagaa       180
gatatggtag ttatacaagg taatgcattc gcgagtagcc atgaagaaat agtacgtgca     240
catcaattga aattagatgt tgtaagttat aatgattttt taggacagat tattgatcaa    300
tatacttcag tagctgtaac tggtgcacat ggtaaaactt ctacaacagg tttattatca    360
catgttatga atggtgataa aaagacttca ttttaattg gtgatggcac aggtatggga    420
ttgcctgaaa gtgattattt cgcttttgag gcatgtgaat atagacgtca cttttaagt    480 tataaacctg attacgcaat tatgacaaat attgatttcg atcatcctga ttattttaaa    540
gatattaatg atgttttga tgcattccaa gaaatggcac ataatgttaa aaaaggtatt    600
attgcttggg gtgatgatga acatctacgt aaaattgaag cagatgttcc aatttattat    660
tatgatttta agattcgga tgacattat gctcaaata ttcaaattac ggataaaggt     720
actgcttttg atgtgtatgt ggatggtgag ttttatgatc acttcctgtc tccacaatat   780
ggtgaccata cagttttaaa tgcattagct gtaattgcga ttagttattt agagaagcta   840
gatgttacaa atattaaaga agcattagaa acgtttggtg tgttaaacg tcgtttcaat    900 gaaactacaa ttgcaaatca agttattgta gatgattatg cacaccatcc aagagaaatt   960
agtgctacaa ttgaaacagc acgaaagaaa tatccacata aagaagttgt tgcagtattt  1020
caaccacaca ctttctctag aacacaagca ttttaaatg aatttgcaga aagtttaagt  1080
```

| aaagcagatc gtgtattctt atgtgaaatt tttggatcaa ttagagaaaa tactggcgca | 1140 |
| ttaacgatac aagatttaat tgataaaatt gaaggtgcat cgttaattaa tgaagattct | 1200 |
| attaatgtat tagaacaatt tgataatgct gttgttttat ttatgggtgc aggtgatatt | 1260 |
| caaaaattac aaaatgcata tttagataaa ttaggcatga aaaatgcgtt ttaa | 1314 |

<210> SEQ ID NO 43
<211> LENGTH: 1482
<212> TYPE: DNA
<213> ORGANISM: Staphylococcus aureus

<400> SEQUENCE: 43

| ttggatgcaa gtacgttgtt taagaaagta aaagtaaagc gtgtattggg ttctttagaa | 60 |
| caacaaatag atgatatcac tactgattca cgtacagcga gagaaggtag catttttgtc | 120 |
| gcttcagttg gatatactgt agacagtcat aagttctgtc aaaatgtagc tgatcaaggg | 180 |
| tgtaagttgg tagtggtcaa taagaacaa tcattaccag ctaacgtaac acaagtggtt | 240 |
| gtgccggaca cattaagagt agctagtatt ctagcacaca cattatatga ttatccgagt | 300 |
| catcagttag tgacatttgg tgtaacgggt acaaatggta aaacttctat tgcgacgatg | 360 |
| attcatttaa ttcaaagaaa gttacaaaaa atagtgcat atttaggaac taatggtttc | 420 |
| caaattaatg aaacaaagac aaaaggtgca aatacgacac cagaaacagt ttctttaact | 480 |
| aagaaaatta agaagcagt tgatgcaggc gctgaatcta tgacattaga agtatcaagc | 540 |
| catggcttag tattaggacg actgcgaggc gttgaatttg acgttgcaat attttcaaat | 600 |
| ttaacacaag accatttaga ttttcatggc acaatggaag catacggaca cgcgaagtct | 660 |
| ttattgttta gtcaattagg tgaagatttg tcgaaagaaa agtatgtcgt gttaaacaat | 720 |
| gacgattcat tttctgagta tttaagaaca gtgacgcctt atgaagtatt tagttatgga | 780 |
| attgatgagg aagcccaatt tatggctaaa atattcaag aatctttaca aggtgtcagc | 840 |
| tttgattttg taacgccttt tggaacttac ccagtaaaat cgccttatgt tggtaagttt | 900 |
| aatatttcta atattatggc ggcaatgatt gcggtgtgga gtaaaggtac atctttagaa | 960 |
| acgattatta aagctgttga aaatttagaa cctgttgaag gcgattaga agttttagat | 1020 |
| ccttcgttac ctattgattt aattatcgat tatgcacata cagctgatgg tatgaacaaa | 1080 |
| ttaatcgatg cagtacagcc ttttgtaaag caaaagttga tatttttagt tggtatggca | 1140 |
| ggcgaacgtg atttaactaa aacgcctgaa atggggcgag ttgcctgtcg tgcagattat | 1200 |
| gtcattttca caccggataa tccggcaaat gatgacccga aaatgttaac ggcagaatta | 1260 |
| gccaaaggtg caacacatca aaactatatt gaatttgatg atcgtgcaga agggataaaa | 1320 |
| catgcaattg acatagctga gcctggggat actgtcgttt tagcatcaaa aggaagagaa | 1380 |
| ccatatcaaa tcatgccagg gcatattaag gtgccacatc gagatgattt aattggcctt | 1440 |
| gaagcagctt acaaaaagtt cggtggtggc cctgttgatt aa | 1482 |

<210> SEQ ID NO 44
<211> LENGTH: 771
<212> TYPE: DNA
<213> ORGANISM: Staphylococcus aureus

<400> SEQUENCE: 44

| atgttttaaaa agctaataaa taaaaagaac actataaata attataatga agaattagac | 60 |
| tcgtctaata tacctgaaca tatcgctatt attatggatg gtaatgggcg atgggctaag | 120 |
| aagcgaaaaa tgcctagaat taaaggtcat tacgaaggta tgcaaacaat aaaaaaaatt | 180 |

```
actagggtag ctagtgatat tggtgttaag tacttaactt tatacgcctt ttccactgaa      240
aattggtcaa gacctgaaag tgaagtaaat tatattatga atttgcctgt caatttctta      300
aagacattct taccggaact aattgaaaaa aatgtcaaag ttgaaacaat tggatttact      360
gataagttgc caaaatcaac gatagaagca attaataatg ctaaagaaaa gacagctaat      420
aataccggct taaaattaat atttgcaatt aattatggtg gcagagcaga acttgttcat      480
agtattaaaa atatgtttga cgagcttcat caacaaggtt taaatagtga tatcatagat      540
gaaacatata taaacaatca tttaatgaca aaagactatc ctgatccaga gttgttaatt      600
cgtacttcag gagaacaaag aataagtaat ttcttgattt ggcaagtttc gtatagtgaa      660
tttatcttta atcaaaaatt atggcctgac tttgacgaag atgaattaat taaatgtata      720
aaaatttatc agtcacgtca aagacgcttt ggcggattga gtgaggagta g               771
```

ANTISENSE MOLECULES FOR TREATMENT OF *STAPHYLOCOCCUS AUREUS* INFECTION

GOVERNMENT INTEREST

This work is based in part by the Defense Advanced Research Project Agency under Phase I SBIR contract number W911 QX-12-C-0072. The US government has certain rights to the invention.

REFERENCE TO SEQUENCE LISTING SUBMITTED ELECTRONICALLY VIA EFS-WEB

The content of the electronically submitted sequence listing (Name: 3344_0040001_SeqListing_Updated.txt; Size: 31,810 bytes; and Date of Creation: Feb. 12, 2016) was originally submitted in the International Application No. PCT/US2014/028855 and is incorporated herein by reference in its entirety.

FIELD OF THE INVENTION

The field of the invention relates to antisense polynucleotide reagents targeting membrane stability proteins useful for treatment of *Staphylococcus aureus* infection.

SUMMARY OF THE INVENTION

Provided are antisense molecules useful for treatment of *Staphylococcus aureus* infection and the inhibition of *Staphylococcus aureus* growth. The antisense molecules target *Staphylococcus aureus* membrane stability proteins and may comprise natural nucleic acid polymers and non-natural nucleic acid polymers, with the proviso that said membrane protein is not FmhB. Non-natural nucleic acid polymers include polymers with modified backbones, such as PNA, PMO, and synthetically-modified DNA and RNA. The invention includes any type of synthetically-modified DNA or RNA that hybridizes to natural DNA and RNA. In one embodiment, the antisense molecules are in the form of a salt or a complex. In one embodiment, the antisense molecule is complexed to a cationic polymeric molecule. In another embodiment, the antisense molecule is conjugated to a cell penetrating molecule. Also provided are pharmaceutical compositions comprising the antisense molecules of the invention.

In one embodiment the invention provides an antisense molecule or salt thereof that inhibits the growth of *Staphylococcus aureus* comprising a polynucleotide sequence that is antisense to the coding region of a *Staphylococcus aureus* membrane stability protein and hybridizes to said coding region under physiological conditions. In one embodiment, the antisense molecule is 10 to 50 nucleobases in length. In another embodiment, the antisense molecule is fully complementary to a coding region of a *staphylococcus aureus* membrane stability protein, with the proviso that said membrane protein is not FmhB. In another embodiment, the antisense molecule is at least 80% identical to a sequence selected from the group consisting of SEQ ID NOS: 1-16. In another embodiment, the antisense molecule is an oligonucleotide. In another embodiment, the antisense molecule is substantially pure. In another embodiment, the antisense molecule comprises a modified backbone. In another embodiment, the modified backbone is a PNA backbone. In another embodiment, the antisense molecule is conjugated to a cell penetration molecule. In another embodiment, the cell penetration molecule is a peptide. In another embodiment, the peptide is a cell penetrating peptide (CPP). In another embodiment, the antisense molecule is complexed to a delivery polymer. In another embodiment, the delivery polymer is a cationic block copolymer comprising phosphonium or ammonium ionic groups.

The invention also provides a method of inhibiting the growth of *Staphylococcus aureus*, comprising administering an antisense molecule or composition of the invention to a tissue containing said *Staphylococcus aureus* or suspected of containing *Staphylococcus aureus*. In one embodiment, the administering is topical administration.

The invention also provides a method of treating *Staphylococcus aureus* infection, comprising administering to an animal in need thereof an effective amount of the antisense molecule or composition of the invention.

BRIEF DESCRIPTION OF THE DRAWINGS

FIG. 4 is a table describing the dosing amounts for a single dose tolerability study of PNA-peptide antisense antibiotic with pharmacokinetic endpoints in mice.

FIG. 5 is a table describing the dosing schedule for a multi-dose safety study of PNA-peptide antisense antibiotic in mice.

BRIEF DESCRIPTION OF THE SEQUENCE LISTING

Figure 1:
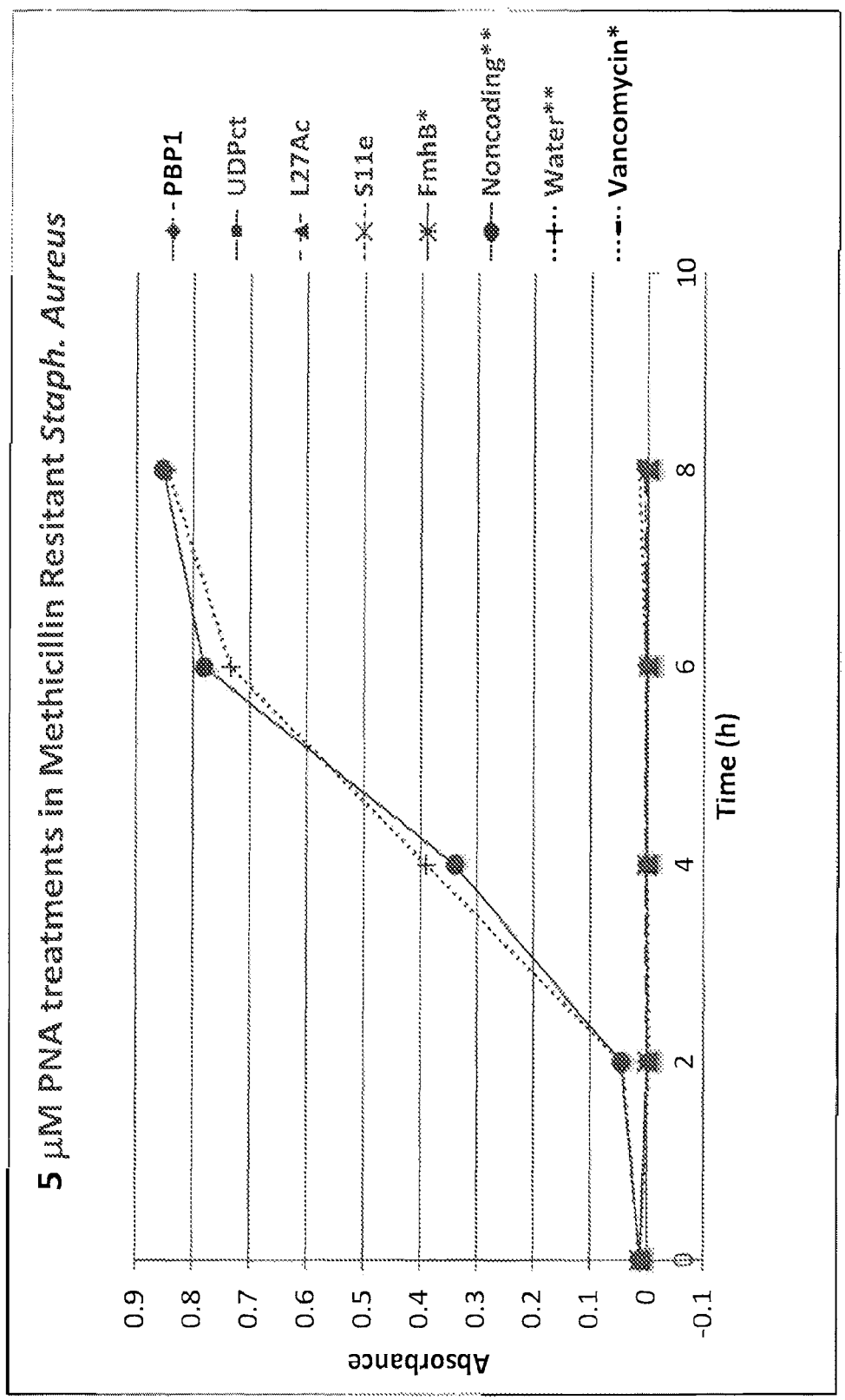
FIG. 1. MRSA in vitro studies. Efficacy of antibacterial nucleic acid agents is demonstrated. Peptide-PNA was tested against bacteria in culture of MRSA USA 300. Vancomycin was used to standardize these results for additional studies.

The polynucleotide sequences in the sequence listing include the coding sequences for *Staphylococcus aureus* membrane stability proteins. See, SEQ ID NOS: 31-44.

The polynucleotide sequences in the sequence listing also include antisense, deoxyribonucleic acids (DNA) and/or modified nucleic acids, such as peptide nucleic acids (PNA). These sequences are capable of knockdown of expression of at least the following *Staphylococcus aureus* membrane stability protein as set forth in Table 1:

TABLE 1

Antisense Polynucleotides Targeting Membrane Stability Proteins

| Protein Target | Antisense Polynucleotide Sequence |
|---|---|
| Alanine racemase | CCGACATATTAC (SEQ ID NO: 6) |
| Cell division protein FtsI (Peptidoglycan synthetase) | CATTACTACGCA (SEQ ID NO: 3) |
| D-alanine--D-alanine ligase | TGTCATTTCGTTTTC (SEQ ID NO: 16) |
| Glutamate racemase | ATTCATATTCGGTCA (SEQ ID NO: 9) |
| Multimodular transpeptidase-transglycosylase/Penicillin-binding protein 1A/1B (PBP1) | TCATACGCGGTC (SEQ ID NO: 5) |
| Multimodular transpeptidase-transglycosylase/Penicillin-binding protein 1A/1B (PBP1) | CGTCATACGCGGTCC (SEQ ID NO: 1) |
| Phospho-N-acetylmuramoyl-pentapeptide-transferase | ACAAAAATCATAACT (SEQ ID NO: 10) |
| Proposed amino acid ligase found clustered with an amidotransferase | GTCTCATGTGTTTCC (SEQ ID NO: 15) |
| tRNA-dependent lipid II-Gly-glycine ligase (FmhB) | TCCATGATTTAT (SEQ ID NO: 30) |
| tRNA-dependent lipid II-Gly-glycine ligase (FmhB) | TTTTCCATGATTTAT (SEQ ID NO: 28) |
| tRNA-dependent lipid II-Gly-glycine ligase @ tRNA-dependent lipid II-GlyGly-glycine ligase @ FemA, factor essential for methicillin resistance | TACTCATTTTATCAA (SEQ ID NO: 12) |
| UDP-N-acetylglucosamine 1-carboxyvinyltransferase | CATCGTAAATCC (SEQ ID NO: 7) |
| UDP-N-acetylglucosamine 1-carboxyvinyltrasferase | ATCCATCGTAAATCC (SEQ ID NO: 2) |
| UDP-N-acetylglucosamine-N-acetylmuramyl-(pentapeptide) pyrophosphoryl-undecaprenol N-acetylglucosamine transferase | TTTCGTCATTAA (SEQ ID NO: 4) |
| UDP-N-acetylglucosamine-N-acetylmuramyl-(pentapeptide) pyrophosphoryl-undecaprenol N-acetylglucosamine transferase | GATTTTCGTCATTAA (SEQ ID NO: 13) |
| UDP-N-acetylmuramate-alanine ligase | AGTGTGTCATTATAT (SEQ ID NO: 14) |
| UDP-N-acetylmuramoylalanyl-D-glutamate-L-lysine ligase | TGCATCCAAACTGAA (SEQ ID NO: 8) |
| Undecaprenyl pyrophosphate synthetase | TTAAACATGGTCTTT (SEQ ID NO: 11) |

The sequence listing also contains control sequences of tRNA-dependent lipid II glycine ligase (FmhB) ttttccatgatttat (SEQ ID NO:28); and Noncoding negative control (NC): aacattttggttttt (SEQ ID NO: 29).

The peptide sequences in the sequence listing include peptides that target and/or localize nucleic acids and nanoparticles to bacterial cells and promote bacterial membrane permeation. See Table 2:

TABLE 2

Cell Penetrating Peptides

| Peptide Name | Amino Acid Sequenct |
|---|---|
| KFF peptide | KFFKFFKFFK (SEQ ID NO: 17) |
| RFF peptide | RFFRFFRFFR (SEQ ID NO: 18) |

TABLE 2 -continued

Cell Penetrating Peptides

| Peptide Name | Amino Acid Sequenct |
|---|---|
| Magainin 2 | GIGKWLHSAKKFGKAFVGEIMNS (SEQ ID NO: 19) |
| Transportin 10 | AGYLLGKINLKALAALAKKIL (SEQ ID NO: 20) |
| Indolicidin | ILPWKWPWWPWRR (SEQ ID NO: 27) |
| TAT peptide | GRKKRRQRRRPQ (SEQ ID NO: 26) |
| PENETRATIN 1 peptide | RQIKIWFQNRRMKWKK (SEQ ID NO: 25) |
| amphipathic peptide | LLIILRRRIRKQAHAHSK (SEQ ID NO: 24) |
| cyclic d,l-alpha-peptide | KQRWLWLW (SEQ ID NO: 23) |
| cyclic d,l-alpha-peptide | RRKWLWLW (SEQ ID NO: 22) |
| cyclic d,l-alpha-peptide | KKLWLW (SEQ ID NO: 21) |

DEFINITIONS

The terms used in this disclosure have ordinary meanings as used in the art.

A polymer is a linear chain of units called monomers. In a polymer, the monomeric units may be identical or they may be different. Polymers may be natural (made in nature) or may be synthetic. Polymers of the present invention comprise nucleic acid polymers, polypeptides, and synthetic delivery polymers.

A nucleic acid is a linear polymer of nucleotides. Nucleic acids made in nature contain deoxyribonucleotide (DNA) bases adenine, cytosine, guanine, and thymine; or ribonucleotide (RNA) bases adenine, cytosine, guanine, and uracil. As used herein, polynucleotide and oligonucleotide refer to a nucleic acid molecule and include genomic DNA, cDNA, RNA, or mRNA of any length. Nucleic acid, polynucleotide, oligonucleotide are terms that may be used interchangeably.

Modified nucleic acids are non-natural polymers that hybridize to natural DNA and RNA with sequence specificity according to Watson-Crick base paring rules. Examples of modified nucleic acids are phosphorothioate-oligodeoxy-nucleotides (PS-ODNs), locked nucleic acids (LNAs), 2'-O-methyloligoribonucleotides (2'O-Mes), phosphorodiamidate morpholino oligonucleotides (PMOs), and peptide nucleic acids (PNAs). Modified nucleic acids have modified backbones and are generally more resistant to degradation than natural nucleic acids. The invention includes any type of synthetically-modified DNA or RNA that hybridizes to natural DNA and RNA. See, e.g., U.S. Pat. Nos. 5,116,195, 5,539,082, 5,527,675, 5,623,049, 5,714,331, 5,736,336, 5,773,571, 5,786,461, 5,811,232, 5,837,459, 5,874,564, 5,891,625, 5,972,610, 5,986,053, 6,107,470, 6,174,870, 7,098,192, 7,696,345, 8,124,745, 8,354,093, 8,357,664, Wagner et al., Nucl. Acid Res. 19:5965-71 (1991); and Koshkin et al., Tetrahedron 54:3607-30 (1998).

Antisense molecules of the invention may also be composed of non-natural polymers that hybridize to natural nucleic acids. A typical nucleoside bases may also be employed, such as methylated bases, phosphorylated bases, inosine, thiouridine, pseudouridine, dihydrouridine, queuosine, and wyosine, among others. Examples of such antisense polymers comprising atypical bases are disclosed in U.S. Pat. Nos. 7,875,733, 7,919,612, 7,939,677, 8,314,229, 8,372,969, and 8,377,898.

The term antisense polynucleotide refers to a nucleic acid molecule that is complementary to at least a portion of a target nucleotide sequence of interest and hybridizes to the target nucleotide sequence under physiological conditions. Antisense molecules specifically hybridize with one or more nucleic acids encoding a preselected target nucleic acid. The terms target nucleic acid and nucleic acid encoding the target encompass DNA encoding the target, RNA (including pre-mRNA and mRNA) transcribed from such DNA, and also cDNA derived from such RNA. The hybridization of an antisense compound with its target nucleic acid interferes with the normal function of the nucleic acid. This modulation of function of a target nucleic acid by compounds which specifically hybridize to it is generally referred to as antisense. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the target. In the context of the present invention, modulation means either an increase (stimulation) or a decrease (inhibition) in the expression of a gene. In the context of the present invention, inhibition is the form of modulation of gene expression.

Polynucleotides are described as complementary to one another when hybridization occurs in an antiparallel configuration between two single-stranded polynucleotides.

The percent identity between the two sequences is a function of the number of identical positions shared by the sequences, taking into account the number of gaps, and the length of each gap, which need to be introduced for optimal alignment of the two sequences. The comparison of sequences and determination of percent identity and similarity between two sequences can be accomplished using a mathematical algorithm (see e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two sequences is determined based on alignments generated with the Clustal W algorithm (Thompson, J. D. et al., 1994, Nucleic acids Res. 22:4673-4680). This algorithm is incorporated into many commercial, software packages, in this case the alignX software program in the Vector NTI suite (version 8.0). Default Clustal W parameters were used to generate pairwise alignments from which percent identity values were calculated (gap opening penalty of 10; gap extension penalty of 0.1). The percent identity is defined as the number of identical bases divided by the total number of bases and multiplied by 100. If sequences in the alignment are of different lengths (due to gaps or extensions), the length of the longest sequence will be used in the calculation, representing the value for total length.

Proteins are polymers containing one or more chains of amino acids bonded together by peptide bonds. Proteins typically fold into a three dimensional form, facilitating a biological function.

A polypeptide is a polymer of amino acids bonded together by peptide bonds. The terms protein and polypeptide and peptide are generally used interchangeably, although polypeptides and peptides are generally shorter in length than proteins.

The terms charged, uncharged, cationic and anionic refer to the predominant state of a chemical moiety at near-neutral pH, e.g. about 6 to 8. In one embodiment, the term refers to the predominant state of the chemical moiety at physiological pH, that is, about 7.4. Thus, a cationic backbone linkage is predominantly positively charged at pH 7.4.

The term substantially pure means that the antisense molecule is substantially free from other materials such as other nucleic acids, proteins, lipids, carbohydrates, and other materials with which it may be naturally associated. In one embodiment, substantially pure antisense molecules are 95-95% homogeneous by HPLC. In another embodiment, substantially pure antisense molecules are 99-100% homogenous by HPLC.

DETAILED DESCRIPTION OF THE INVENTION

The present invention may be understood by reference to the following detailed description of the embodiments of the invention and examples included herein. The terminology used herein is for the purpose of describing embodiments of the invention and is not, intended to be limiting.

Specific aspects of the invention include antisense molecules that are useful for the treatment of *Staphylococcus aureus* infection and/or inhibit the growth of *Staphylococcus aureus* comprising an antisense molecule that is antisense to a *Staphylococcus aureus* membrane stability protein coding region under physiological conditions. In one embodiment, the antisense molecule hybridizes to a *Staphylococcal aureus* membrane stability coding region selected from the group consisting of SEQ ID NOS: 31-44. In one embodiment, the antisense molecule contains 10-50 nucleobases, i.e., is a 10-50-mer. In another embodiment, the antisense molecule is a 10-25-mer, a 12-20-mer, a 12-15-mer, a 11-mer, a 12-mer, a 13-mer, a 14-met, a 15-mer, a 16-mer, a 17-mer, an 18-mer, a 19-mer, a 20-mer, a 21-mer, a 22-mer, a 23-mer, a 24-mer, a 25-mer, a 26-mer, a 27-mer, a 28-mer, a 29-mer, or a 30-mer. The nucleotide sequence for the antisense molecule is chosen at a binding location that preferably spans the start codon. Proprietary software scans window sizes 10 bases, 11 bases, 12 bases, 13 bases, 14 bases, 15 bases, 16 bases, 17 bases, 18 bases, 19 bases, and/or 20-40 bases (as a non-limiting example) including the start codon and ranks self-folding potential by base content. The software algorithm may be programmed to span the start codon. Alternatively, the algorithm may be programmed to optionally span the start codon region. Selection of antisense sequence can be finalized manually from these data or through an automated process derived from empirical data and parameter weighting. These antisense molecules against membrane stability protein-expressed genes are substantially orthogonal to the human transcriptome. In one embodiment, the antisense molecules have base lengths exhibiting features such as Tm greater than 37° C., low self-folding, and significant start codon overlap.

In another embodiment, the invention provides a polynucleutide sequence at least 80% identical to a sequence selected from SEQ ID NO: 1-16. Specifically, the sequences may contain one or more substitutions, additions, deletions, and/or insertions with natural or non-natural nucleotides, such that the target gene modulation activity is not substantially diminished. Variants exhibit at least about 80%, 81%, 82%, 83%, 84% 85%, 86%, 87%, 88%, or 89% sequence identity; and another embodiment at least about 90%, 91%, 92%, 93%, 94%, 95%, 96%, 97%, 98%, or 99% identity to a sequence selected from the group consisting of SEQ ID NOS: 1-16. The percent identity may be readily determined by comparing sequences of the polynucleotides to the corresponding portion of the target polynucleotide, using any method including using computer algorithms well known to those of ordinary skill in the art. Algorithms include the Align or the BLAST algorithm (Altschul, 1991 *J. Mol. Biol.* 219:555-565; Henikoff and Henikoft, 1992, Proc. Natl. Acad. Sci. USA 89:10915-10919).

In one embodiment of the invention, the active ingredient is coupled to a targeting/cell penetration molecule. In one aspect of the invention, the targeting molecule comprises a peptide. The peptide may comprise a cell penetration peptide (CPP). Peptides utilized may have one or more functions to facilitate cell targeting and/or membrane permeation. In particular, the therapeutic polynucleotides of the invention can be delivered to *Staphylococcus aureus* in a host by conjugating peptides to the antisense molecule. The ability to conjugate antisense molecules to peptides for membrane disruption of bacteria provides specificity and reduces toxicity. Examples of cell penetration peptides include those having SEQ ID NOS: 17-27. Additional examples cell penetration peptides and methods to link them to antisense molecules are described in U.S. Pat. Nos. 8,354,387, 8,354, 093, 8,313,778, 8,299,236, 8,242,081, 8,211,468, 8,207,293, 8,138,383, 8,044,019, 8,039,587, 7,943,581, and 7,879.813. In another embodiment, the cell penetrating peptides is derived from HIV tat, herpes virus VP22, the Drosphila Antennapedia homeobox gene product, signal sequences, fusion sequences or protegrin I as disclosed in U.S. Pat. No. 8,338,366. The antisense molecule-peptide conjugate may be prepared by methods of solid-phase synthesis, where cysteine serves as the linker between peptide and DNA. Other methodologies known in the art may be used (See for example, Dirksen, A., et al., *J Am. Chem. Soc.* 2006. 128, 15602-3).

CPPs useful in the invention are peptides of diverse origins. Cationic nucleic acid-carrier peptides form productive nanoparticles when mixed with the synthetic polymers of the invention. One example is the peptide KFFKFFKFFK (SEQ ID NO: 17) described in Xie et al., *Molecular Therapy* 2004, 10, 652-659. Additional peptides may include TAT peptide and PENETRATIN. The TAT peptide, GRK-KRRQRRRPQ (SEQ ID NO: 26), is derived from the transactivator of transcription (TAT) of human immunodeficiency virus and is a CPP. CPPs overcome the lipophilic barrier of cell membranes and deliver large molecules and particles inside the cell for their biological actions. PENETRATIN peptide is a 16-amino acid peptide of sequence RQIKIWFQNRRMKWKK (SEQ ID NO: 25) corresponding to the third helix of the homeodomain of Antennapedia protein.

Useful CPPs also encompass cyclic d,1-αpeptides, such as, KQRWLWLW (SEQ ID NO: 23), RRKWLWLW (SEQ ID NO: 22), and KKLWLW, (SEQ ID NO: 21) as described in Fernandez-Lopez et al., *Nature* 2001, 412, 452-455. These peptides have antibiotic properties of their own, and also function as carriers of cargo for internal cellular delivery. Additionally, amphipathic peptides LLIILRRRIRKQA-HAHSK (SEQ ID NO: 24) and transportin 10 (TP10), AGYLLGKINLKALAALAKKIL (SEQ ID NO: 20), described in Nekhotiaeva et al. *FASEB J.* 2010, 394-396, form productive nanoparticles. Tryptophan, rich peptides, such as Magainin 2 peptide, GIGKWLHSAKKFGKAF-VGEIMNS (SEQ ID NO: 19), which was isolated from the African clawed frog (Karas et al, *Biochemistry* 2002, 41, 10723-31), are additional CPPs useful in the present invention. Furthermore, Indolicidin, ILPWKWPWWPWRR (SEQ ID NO: 27), which was isolated from bovine neutrophils, is another CPP useful in the present invention. These and other peptides of similar sequence and properties are recognized by one of skill in the art as functional alternatives and are encompassed by the present invention. Furthermore, these peptides may be modified to improve function as desired or needed.

Bulk peptide and polynucleotide synthesis can be carried out by contract manufacturers, such as Neo Group, Inc. (Cambridge, Mass.) using standard methodologies including solid-scaffold protection/deprotection synthesis via high fidelity synthesizers. The peptide-PNA or peptide-DNA component is the therapeutic molecule which enters the pathogen and disrupts its genetic regulation.

In one embodiment, an antisense molecule is conjugated to a CPP using well known conjugation methods that employ succinimidyl-6-hydrazinonicotinateacetonehydrazone to succinimidyl-4-formylbenzoate coupling chemistry. This is a specific, well-behaved, and highly efficient conjugation method for peptide-DNA coupling. In order to covalently couple peptides to nucleic acids, the peptides are prepared for reaction by modifying the N-terminal with a reactive group. In one embodiment, the N-terminal of the peptide is modified with S6H (succinimidyl-6-hydrazinonicotinateacetonehydrazone). N-protected peptides are desalted and dissolved in dry DMF. Next, S6H is added in 2× molar excesses to a stirring solution and allowed to react at room temperature for 2 hours. Workup follows procedures known in the art, such as that described by Dirksen et al. *J. Am. Chem. Soc.* 2006 128, 15602-3. Other methods of coupling peptides to nucleic acids known in the art may be used.

Figures 2A, 2B:
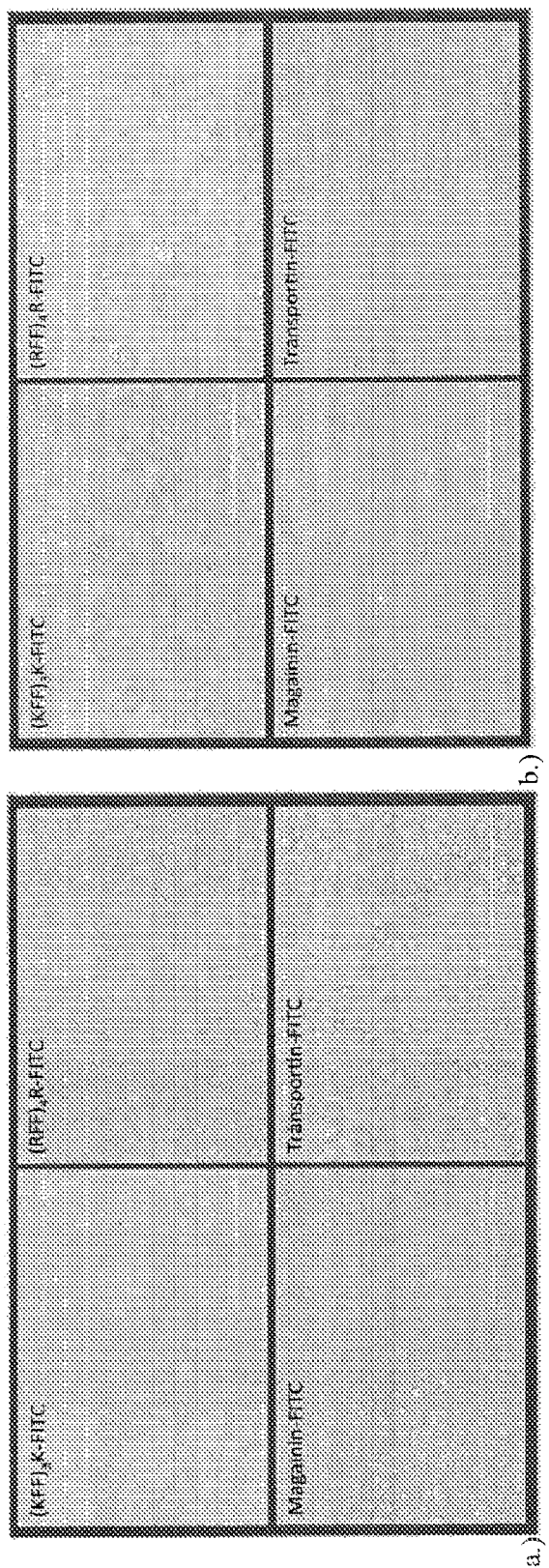
FIG. 2A-2B. a) MRSA fluorescent overlays 2 hours post treatment with 1 uM of FITC-peptide agents. b) AcB fluorescent overlays 2 hours post treatment with 1 uM of FITC-peptide agents. Scale bar=100 um. This figure shows that the cell-penetrating peptides are non-toxic when used alone.
Figure 3:
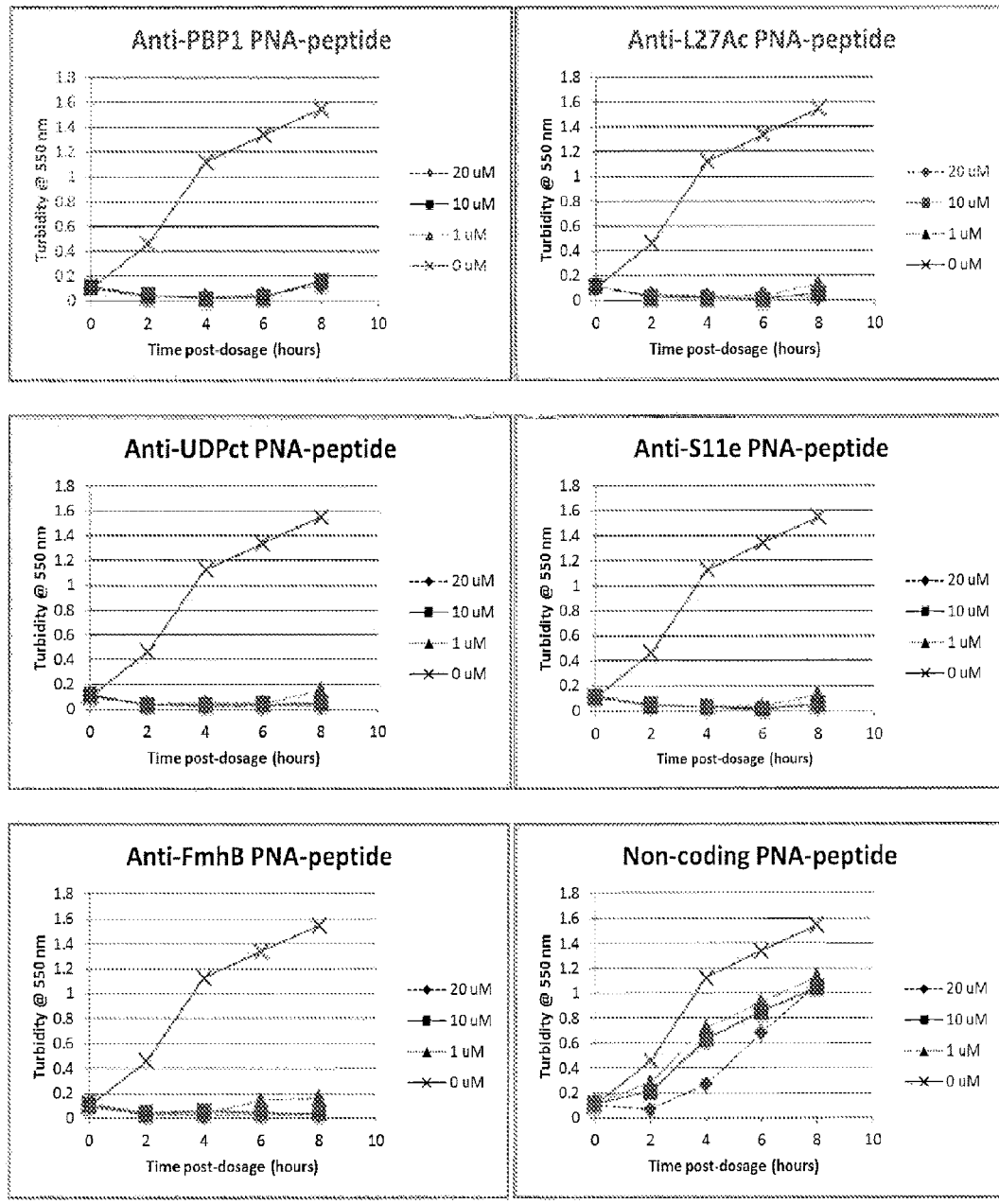
FIG. 3. Shows log-phase MRSA growth inhibition over 8 hours at 0 μM, 1 μM, 10 μM, and 20 μM concentration of PNA-peptide antisense antibiotic. Bottom left represents a positive control (FmhB) and bottom right shows a negative control.

An FITC assay may be utilized to monitor cellular uptake of peptides. Peptides were conjugated to fluorescein isothiocyanate (FITC) to monitor uptake using florescence microscopy. FIG. 2A-2B show assay results for several peptides as tested in MRSA (FIG. 2A) and AcB (FIG. 2B) (fluorescent overlays 2 hours post-treatment with 1 µM of FITC-peptide agents, scale bar=100 µm). For MRSA, the helical cationic peptides with KFF and RFF motifs are effective for cellular entry. Also, Magainin-FITC is effective for entry into MRSA. There do not appear to be any bactericidal effects from the peptides at the tested concentration (1 µM) in any of the micrographs presented in FIG. 2A-2B.

In another embodiment of the invention, the antisense molecule is combined with a delivery polymer. The polymer-based nanoparticle drug delivery platform is adaptable to a diverse set of polynucleotide therapeutic modalities. In one aspect of the invention, the delivery polymer is cationic. In another aspect of the invention, the delivery polymer comprises phosphonium ions and/or ammonium ions. In another example of the invention, the antisense molecule is combined with a delivery polymer, and the composition forms nanoparticles in solution. In a further embodiment, nanoparticle polyplexes are stable in serum and have a size in the range of about 30 nm-5000 nm in diameter. In one embodiment, the particles are less than about 300 nm in diameter. For example, the nanoparticles are less than about 150 nm in diameter.

In one embodiment, the delivery vehicle comprises a cationic block copolymer comprising phosphonium or ammonium ionic groups as described in PCT/US12/42974. In one embodiment, the polymer is diblock-Poly[(ethylene glycol)$_9$ methyl ethyl methacralate][stirylphosphonium]. In another embodiment of the invention, the delivery polymer comprises glycoamidoamines as described in Tranter et al. *Amer Soc Gene Cell Ther*, December 2011; polyhydroxylamidoamines, dendritic macromolecules, carbohydrate-containing polyesters, as described in US20090105115; and US20090124534. In other embodiments of the invention, the nucleic acid delivery vehicle comprises a cationic polypeptide or cationic lipid. An example of a cationic polypeptide is polylysine. See U.S. Pat. No. 5,521,291.

In one embodiment, the antisense molecules are part of a composition comprising delivery or carrier polymers. In another embodiment, the antisense molecules are part of nanoparticle polyplexes capable of transporting antisense molecules with stability in serum. The polyplex compositions comprise a synthetic delivery polymer (carrier polymer) and biologically active compound associated with one another in the form of particles having an average diameter of less than about 500 nm, such as about 300 nm, or about 200 nm, preferably less than about 150 nm, such as less than about 100 nm. The invention encompasses particles in the range of about 40 nm-500 nm in diameter.

In one embodiment, the delivery or carrier polymer comprises a cationic block copolymer containing phosphonium or ammonium ionic groups as described in PCT/US12/42974. In another embodiment of the invention, the delivery or carrier polymer comprises glycoamidoamines as described in Tranter et al. *Amer Soc Gene Cell Ther*, December 2011; polyhydroxylamidoamines, dendritic macromolecules, carbohydrate-containing polyesters, as described in U S20090105115; and US20090124534. The polyglycoamidoamine (PGAA) polymer system, which is a proprietary, localized and biodegradable nanoparticle system, represents another delivery or carrier polymer. Poly(galactaramidoamine) is an efficient cationic polymeric vehicle with low cytotoxicity (Wongrakpanich et al. *Pharmaceutical Development and Technology*, Jan. 12, 2012). The nanoparticle delivery system disclosed in Hemp et al. *Biomacromolecules*, 2012 13:2439-45 represents another delivery or carrier polymer useful in the present invention.

In other embodiments of the invention, the delivery or carrier polymer comprises a cationic polypeptide or cationic lipid. Polymers, such as poly-L-lysine (PLL), polyethyleneimine (PEI), chitosan, and their derivatives are also encompassed by the invention. Nucleic acid delivery using these compounds relies on complexation driven by electrostatic interactions between the gene and the polycationic delivery agent. Polymer-DNA complexes condense into particles on the order of 60 nm-120 nm in diameter. Polymers such as linear PEI and PLL have high transfection rates in a variety of cells.

In vivo nucleic acid delivery has size constraints requiring a sufficiently small polyplex to enable long circulation times and cellular uptake. In addition, polyplexes must resist salt- and serum-induced aggregation. Serum stability is generally associated with a particle size of about sub-150 nm hydrodynamic radius or below maintainable for 24 h. The nanoparticles of the invention, which comprise nucleic acid therapeutic and delivery polymer, have the hydrodynamic radius and material properties for serum stability. In particular, the delivery polymer, when combined with the nucleic acid, protects the therapeutic cargo under physiological conditions. The delivery polymers are designed to have characteristics of spontaneous self-assembly into nanoparticles when combined with polynucleotides in solution.

The invention also contemplates other delivery polymers that form serum-stable nanoparticles. The invention is not limited to the type of delivery polymer and may be adaptable to nucleic acid characteristics, such as length, composition, charge, and presence of coupled peptide. The delivery polymer may also be adaptable for material properties of the resultant nanoparticle, such as hydrodynamic radius, stability in the host bloodstream, toxicity to the host, and ability to release cargo inside a host cell.

In one embodiment, the antisense molecule or penetrating peptide conjugate thereof is administered in the form of a salt. The salt may be any pharmaceutically acceptable salt comprising an acid or base addition salt. Examples of pharmaceutically acceptable salts with acids include those formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulionates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997). Acid addition salts of basic antisense molecules may be prepared by contacting the free base forms with a sufficient amount of the desired acid to produce the salt according to methods and techniques with which a skilled artisan is familiar.

Pharmaceutically acceptable base addition salts are formed by addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like.

The antisense molecules are administered as part of a pharmaceutical composition comprising a pharmaceutically acceptable diluent, excipient or carrier. Suitable diluents, excipients and carriers are well known in the art and are described, for example, in Remington's Pharmaceutical Sciences, Mack Publishing Co. (A. R. Gernnaro Ed., 1985). The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the antisense molecule in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The invention also provides a method of treating *Staphylococcus aureus* infection and a method of inhibiting the growth of *Staphylococcus aureus*. In one embodiment, the *Staphylococcus aureus* is a methicillin-resistant (MRSA) strain. In one embodiment, the animal undergoing treatment for *Staphylococcus aureus* infection exhibits one or more symptoms of *Staphylococcus aureus* infection including puss production in the infected area, boils, abscesses, carbuncles, stys, and/or cellulitis. The animal may also exhibit signs of sepsis or pneumonia.

In one embodiment, the antisense molecules are administered by intravenous, intramuscular, or peritoneal injection. In another embodiment, the antisense molecules are administered topically, e.g. to a tissue suspected to be infected by *Staphylococcus aureus*. In another embodiment the antisense molecules are administered orally. When administered orally, the antisense molecules may be formulated as part of a pharmaceutical composition coated with an enteric coating that will protect the antisense molecules from the acid environment of the stomach and release the antisense molecules in the upper gastrointestinal tract. In another embodiment, the antisense molecules may be formulated as part of a sustained release formulation that will release the antisense molecules on a substantially continuous basis over a period of time.

Animals that may be treated with the antisense molecules according to the invention include any animal that may benefit from treatment with the antisense molecules. Such animals include mammals such as humans, dogs, cats, cattle, horses, pigs, sheep, goats and the like.

The antisense molecules are administered in an amount that is effective for the treatment of *Staphylococcus aureus* infection or inhibition of the growth of *Staphylococcus aureus*. The amount may vary widely depending on the mode of administration, the age of the animal, the weight of the animal, and the surface area of the mammal. The amount of antisense molecule, conjugate, salt and/or complex thereof may range anywhere from 1 pmol/kg, to 1 mmol/kg. In another embodiment, the amount may range from 1 nmol/kg to 10 mmol/kg. When administered topically, the amount of antisense molecule, conjugate, salt and/or complex thereof may range anywhere from 1 to 99 weight percent. In another embodiment, the amount of antisense molecule, conjugate, salt and/or complex thereof may range anywhere from 1 to 10 weight percent.

Example I

Synthesis of Peptide-PNA Conjugate

All PNA agents were prepared using heterogenous solid-phase peptide synthesis techniques and purified with HPLC. Although direct dosing with naked polynucleotides has been used to inhibit pathogenesis of MRSA in culture, a significant barrier for nucleic acid therapy in humans is the bacterial cell wall. To overcome the cell wall barrier, peptides derived from bacterial infecting organisms that can penetrate these bacterial cell walls can be attached to nucleic acids or modified nucleic acids to enhance nucleic acid entry into the bacterium.

DNA sequences were synthesized using high-fidelity synthesizers made by NEO-Bio Group, Cambridge, Mass. The polynucleotide was then coupled to peptides which permit permeation of bacterial membranes and polynucleotide entry. In the present invention, solid-phase synthetic methodology for peptide-DNA coupling was employed where cysteine served as the linker between peptide and DNA.

In a specific embodiment, antisense 15-mer DNA and PNA analogs were synthesized for testing in cell culture. A positive control from literature (FmhB); and a noncoding sequence for use as a negative control (NC) was also synthesized. Each polynucleotide was coupled to the cell penetrating peptide (CPP) motif KFFKFFKFFK (SEQ ID NO: 17).

Both PNA-CPP and DNA-CPP candidates were synthesized and tested. Mass spectrometric analysis of each conjugate was performed to confirm successful synthesis. The purity of the PNA-peptide and DNA-peptide candidates was established using HPLC. Purity of about 99.9% was achieved for PNA-peptide; while >87% was achieved for DNA-peptide. DNA-peptides yielded a higher degree of impurity likely due to the steps required to make the DNA and CPP peptide separately and then conjugate, them before a final purification step. Conversely, synthesis of the PNA agents yielded purity levels of about 99%. Increased purity and simplicity of manufacture of PNA-peptide therapeutics provides advantages over DNA-peptide candidates with respect to cGMP-compliant manufacture in battlefield arenas.

Example II

An FITC assay was utilized to monitor cellular uptake of peptides. Peptides, were conjugated to fluorescein isothiocyanate (FITC) to monitor uptake using florescence microscopy. FIG. 2A-2B shows assay results for several peptides as tested in MRSA (FIG. 2A) and AcB (FIG. 2B) (fluorescent overlays 2 hours post-treatment with 1 µM of FITC peptide agents, scale bar=100 µM). For MRSA, the helical cationic peptides with KFF and RFF motifs are effective for cellular entry. Also, Magainin-FITC is effective for entry into MRSA. There do not appear to be any bactericidal effects from the peptides at the tested concentration (1 µM) in any of the micrographs presented in FIG. 2A-2B.

Example III

MRSA In Vitro Studies

Demonstration of sequence-specific effects of PNA-peptide molecules on MRSA was carried out in MRSA USA 300. MRSA USA 300 is a major source of community-acquired infections in the US, Canada and Europe. Clone FPR3757 is a multidrug-resistant USA 300 strain that is available from ATCC as both the culture (ATCC® BAA-1556™) and the genomic DNA (ATCC® BAA-1556D-5). MRSA USA 300 strain is well characterized which allows for reliable benchmarking. MRSA growth curves were generated by inoculating freshly thawed frozen bacterial stocks at different dilutions ranging from 1:3000, 1:1500, 1:600 and 1:300 in Tryptic Soy Broth (TSB, Becton-Dickinson). Absorbance readings are taken hourly at 600 nm ($A_{600}$) and 550 nm ($A_{550}$) using a Biomate 3S spectrophotometer (Thermo Scientific) to establish optimal measurement settings and characterize bacterial growth kinetics. Readings at 550 nm give slightly higher sensitivity. There is a correlation seen with the lower dilution titrations and a faster time to higher absorbance value. A550 is established as the optimal measurement to assess propagation in vancomycin titration and Minimum Inhibitory Concentration (MIC) assays.

Vancomycin titrations were established to determine a suitable test range. An 800 µg/ml stock solution was diluted tenfold in TSB to 80 µg/ml and further serial diluted to 40, 20, 10, 5, and 2.5 µg/ml in TSB, respectively. MRSA USA 300 strain was cultured to an, early log phase OD 550 value of 0.111 and treated with the 80-2.5 µg/ml range of vancomycin. Absorbance measurements at 550 nm were taken hourly over a 4-hour time period.

Minimum inhibitory concentration (MIC) analyses were performed as described in Clinical and Laboratory Standards Institute. *Methods for Dilution Antimicrobial Susceptibility Tests for Bacteria that Grow Aerobically,* 7th ed.; Approved Standard M7-A7; CLSI: Wayne, Pa., USA, 2006; volume 26, No. 2. Vancomycin and methicillin were used as controls. MIC was determined as the lowest concentration of agent that inhibits bacterial growth detected at $A_{600}$.

Time-kill analyses were performed as described in Haste et al. *J Antibiot.* 2010, 63, 219-224. Agents at various concentrations were aliquoted into the Falcon tubes. Four ml of bacteria at 5E5 cfu/ml were added to the tubes. Tubes were incubated in a shaker at 37° C., and at 0, 2, 4, and 8 h are subsequently analyzed for bacterial growth via $A_{600}$.

Sequence-specific effects of polynucleotide-peptide agents against MRSA: A wide range of concentrations were tested for the PNA-peptide antisense sequences determined from bioinformatics. FmhB was used as a positive control from the literature (Xie et al., *Molecular Therapy,* 2004, 10, 652-659) and a non-encoding sequence with a terminal (KFF)$_3$K motif was used as a negative control (NC) to indicate bactericidal effects imparted by peptide membrane disruption. Sequence-specific inhibition was demonstrated by treating bacteria during lag phase to determine growth inhibition and potential recovery at later time points. The candidate agents and non-coding sequence control were diluted in a range from 20 µM, 5 µM, 1 µM, 250 µM, and 25 µM with sterile RNase-free, DNase-free water. Inhibition of MRSA growth was observed over a wide range of PNA-peptide concentrations.

The time course was carried out using MRSA strain USA 300. Freshly-thawed MRSA at a 1:100 dilution in TSB is added to wells containing the individual PNA-peptide molecules. An additional positive control, vancomycin at 12.5 ug/ml, and a negative control, water only, were also assayed. The samples were allowed to incubate at 37° C. with 225 RPM orbital shaking and measured at two-hour time intervals, over an 8-hour time course. It inhibition of MRSA growth was observed over time at a 5 µM concentration.

In log-phase growth, inhibition was observed at concentrations as low as ~1 µM for PNA-peptide conjugates and as low as ~10 µM for DNA-peptide conjugates.

When cell-penetrating peptides were conjugated to FITC and added to cells in culture, the cells remained alive over time periods of the cell culture experiments.

Example IV

To dissolve the DNA-peptide conjugates, they were dispersed in tris buffer at an elevated pH=9. The conjugates were then gently agitated for 24 h at 40° C. After this time period cloudiness was still observed, so the conjugates were heated to 80° C. under gentle agitation for an additional 6 h, after which clear solutions were obtained. The initial solution is tested via DLS to look at for potential self-assembly between the DNA-peptide conjugates. As exhibited with many charged polymers there was self-aggregation observed in solution, showing broad polydisperse aggregates in the 300 nm to 1-micron range.

Particle size plays an important role in determining blood circulation time and clearance. It is also a predictor of tissue permeation, clearance potential, and selectivity. Polymer-containing particles have been validated with siRNA and DNA, are capable of protecting nucleic acids from nuclease degradation, and can be engineered for colloidal stability in the bloodstream. The antisense molecule; peptide conjugates of the present invention were combined with serum-stable phosphonium-block copolymers to form polyplexes. This diblock copolymer forms a supramolecular assembly with negatively-charged DNA. The particle forms a core-shell type morphology with a neutral polyethylene glycol (PEG) brush on the surface. Polyplex hydrodynamic diameter is measured on a Zetasizer (Nano ZS) dynamic light scattering (DLS) instrument (Malvern Instruments, Worcestershire, UK). As a size comparison, a DNA-peptide conjugate without carrier polymer, was measured at 1 mg/ml in tris buffer solution at pH=9. This DNA-peptide conjugate with diblock-Poly[(ethylene glycol)$_9$ methyl ethyl methacralate] [stirylphosphonium] at three concentrations exhibited size ranges from 40 nm-300 nm.

Formation of nanoparticles with the DNA-peptide conjugates was dependent on physical factors. Because the DNA region is negatively charged and the KFFKFFKFFK (SEQ ID NO: 17) region is positively charged, the conjugates exhibit strong intramolecular associations in solution. A wide range of formulation conditions were evaluated. Optimal particles form at charge-to-charge ratios of 2-4 (phosphonium+/DNA phosphate−) and [DNA-peptide conjugate] ≤0.5 mg/ml and lower. When concentrations exceeded 0.5 mg/ml, dynamic light scattering (DLS) analysis indicated that large aggregates form. The DLS data indicates that pre-formulation concentration influences the final nanoparticle size range, with 0.5 mg/nil forming the largest nanoparticles clustering around 90 nm-100 nm; and 0.1 mg/ml forming particles as small as 40 nm diameter.

To dissolve the DNA-peptide conjugates, they were dispersed in tris buffer at an elevated pH=9. The conjugates were then gently agitated for 24 h at 40° C. After this time period cloudiness is still observed, so the conjugates were heated to 80° C. under gentle agitation for an additional 6 h, after which clear solutions are obtained. The initial solution was tested via DLS to look at for potential self-assembly between the DNA-peptide conjugates. As exhibited with many charged polymers there was self-aggregation observed in solution, showing broad polydisperse aggregates in the 300 nm to 1 µm range.

Example V

To assess the safety of PNA-peptide antisense antibiotic, a single dose tolerability study in mice was performed. As shown in FIG. 4, mice were divided into four groups of 15 animals per group. Each group was given a single intravenous injection of either vehicle control (PBS) or PNA-peptide antisense antibiotic at a dose of 1 mg/kg, 3.3 mg/kg, or 10 mg/kg.

After the injections, sera and tissues were collected as indicated in FIG. 4. Samples were collected 15 min., 30 min., 1 hour, 4 hours, and 12 hours after administration of the PNA-peptide antisense antibiotic. These samples can be assessed for biological safety markers and PNA-peptide antisense antibiotic biodistribution analyses.

Animals were observed for outward signs of toxicity after the injections. All animals survived the treatments and showed no outward signs of toxicity. These results indicate that the PNA-peptide antisense antibiotic is safe in vivo when administered in a single dose as high as 10 mg/kg.

Example VI

To further assess the safety of PNA-peptide antisense antibiotic, multi-dose safety studies were performed in mice. Mice were divided into four groups of 10 animals per group. Each group was given multiple intravenous injections of either vehicle control (PBS) or PNA-peptide antisense antibiotic according to the dosing schedule shown in FIG. 5.

After the injections, animals were monitored for outward signs of toxicity, such as body weight, appetite, and grooming. Depending on the treatment group, animals were sacrificed after three, four, or seven days and blood samples were collected to measure liver and kidney biological markers (FIG. 5).

Figure 6:
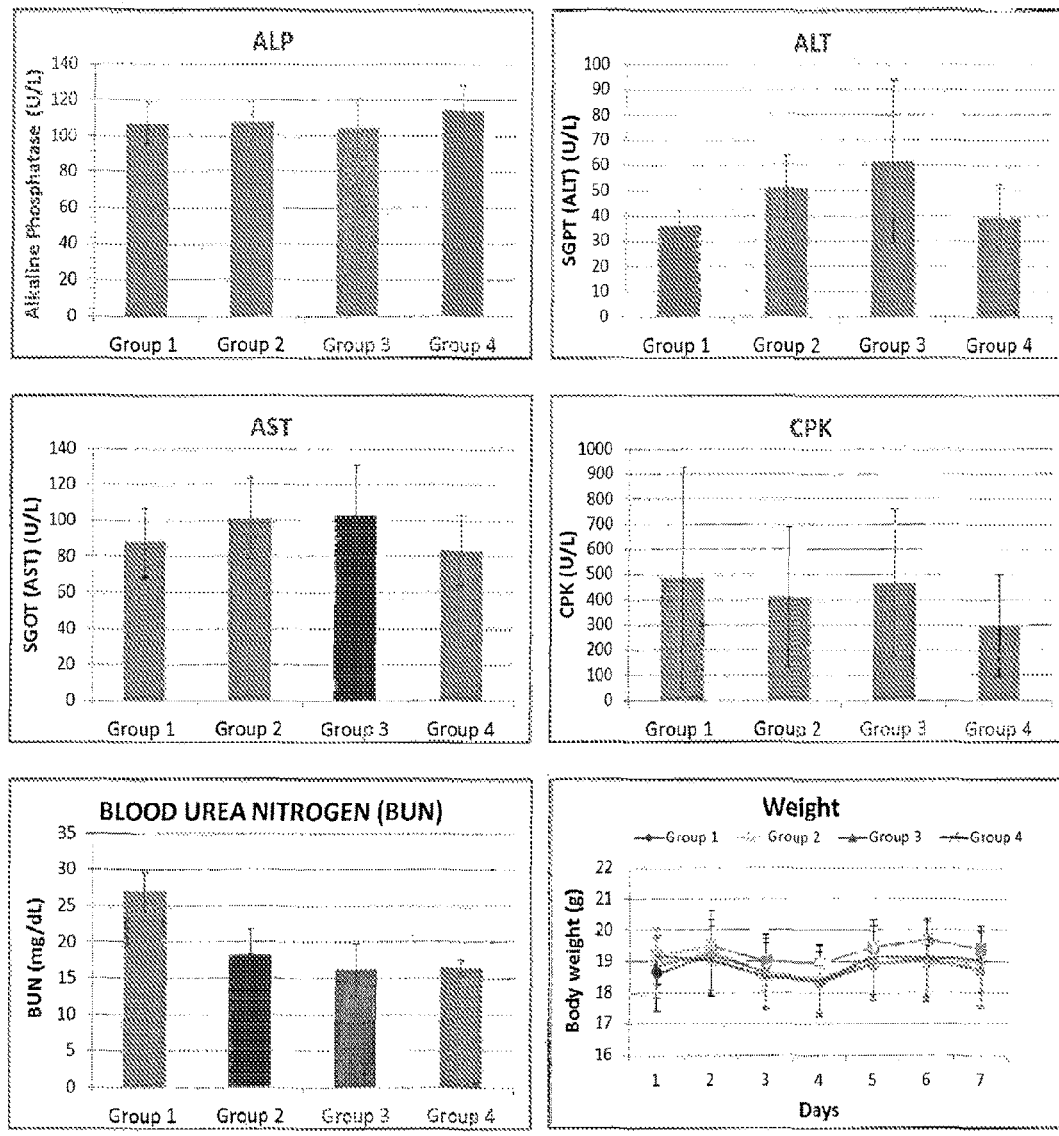
FIG. 6 Shows bar graphs of safety data for multiple doses of PNA-peptide antisense antibiotic in mice. Liver markers (ALP, ALT, AST, CPK), kidney markers (BUN), and body weights of the mice were assessed after multi-dose administration. Bar graphs: liver and kidney markers. Line graph: animal body weight.

No mortality was observed in any treatment group. All animals showed normal appetite and grooming behavior. Furthermore, no significant changes in body weights were observed for any treatment group (FIG. 6). Liver (ALT, ALP, AST, CPK) and kidney (BUN) markers appeared normal in all treatment groups. These results indicate that the PNA-peptide antisense antibiotic is safe in vivo when administered in multiple doses as high as 10 mg/kg.

Example VII

Figure 7:
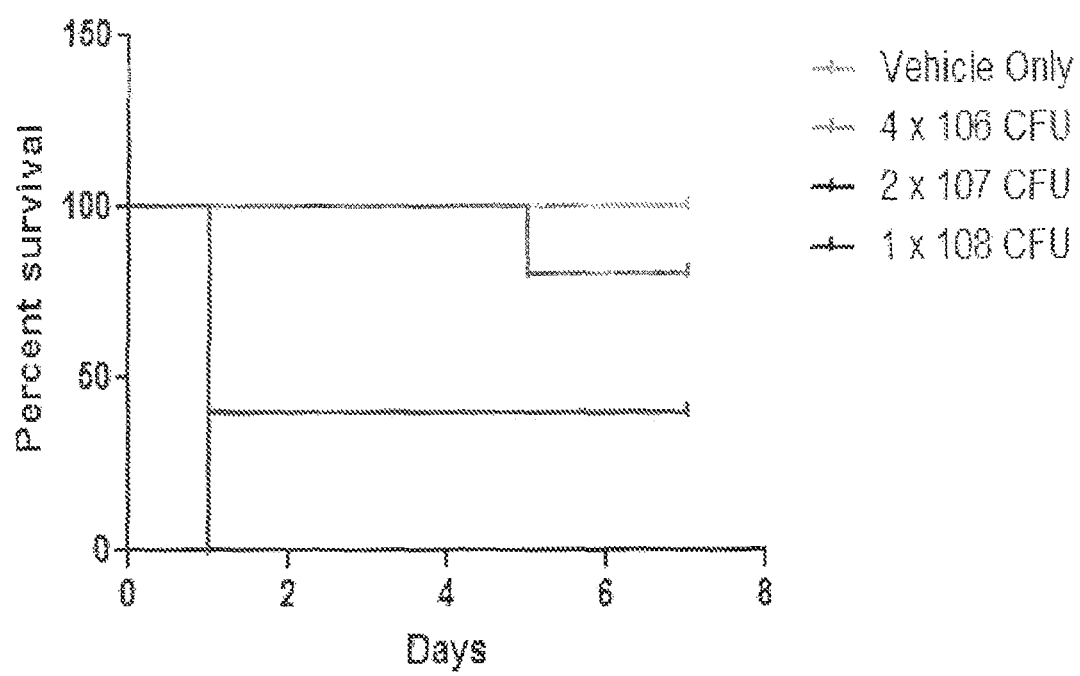
FIG. 7 Shows a line graph of survival data in a model of *S. aureus* blood infection in mice.

To assess the in vivo efficacy of the PNA-peptide antisense antibiotic, a *Staphylococcus aureus* blood infection mouse model was developed. FIG. 7 shows the survival data for mice administered increasing doses of methicillin resistant *S. aureus* (MRSA). Mice were administered either a vehicle control (4% hog, gastric mucin) or $4 \times 10^6$, $2 \times 10^7$, or $1 \times 10^8$ colony forming units (CFU) of MRSA. As shown in FIG. 7, the $LD_{50}$ in this mouse model was approximately $2 \times 10^7$ CFU.

After establishing the blood infection mouse model, the efficacy of the PNA-peptide antisense antibiotic was assessed. Mice were divided into three groups of 10 animals per group. Each group was intravenously injected with MRSA in a volume of 0.2 ml at a concentration of $2 \times 10^7$ CFU/ml. Each group was then treated with (i) vehicle control (PBS); (ii) PNA-peptide antisense antibiotic at a dose of 10 mg/kg; or (iii) vancomycin (2 mg/kg), which served as a positive control. PNA-peptide antisense antibiotic treatments were administered twice daily for four days.

Figure 8:
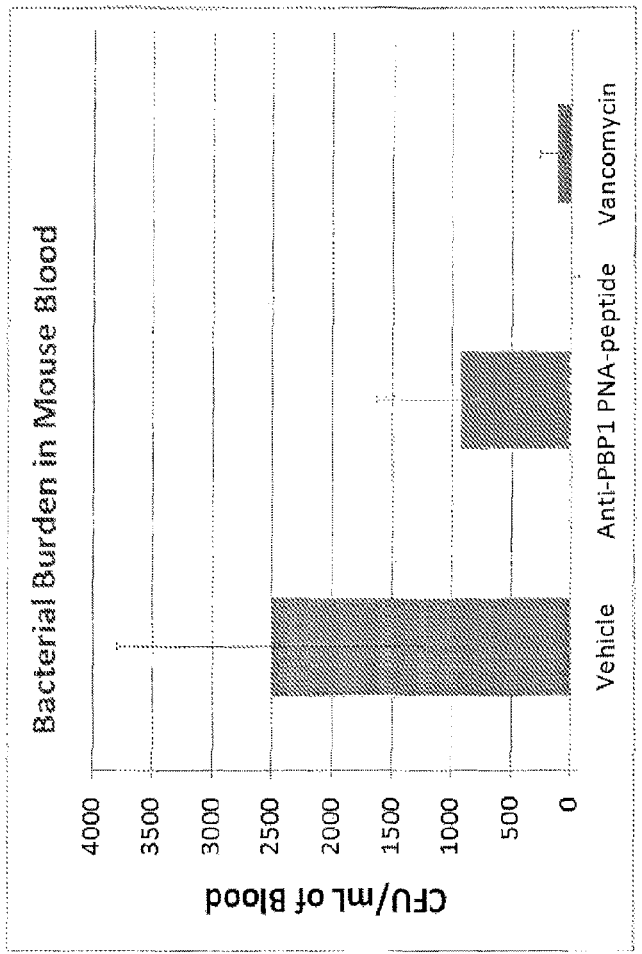
FIG. 8 Shows the in vivo efficacy of the PNA-peptide antisense antibiotic. The table describes the dose and treatment regimen for mice that were injected with MRSA and PNA-peptide antisense antibiotic. The bar graph shows bacterial burden in mouse blood 24 hours after treatment.

FIG. 8 shows the bacterial burden in mouse blood 24 hours after treatment. As shown in FIG. 8, treatment with the PNA-peptide antisense antibiotic reduced the levels of MRSA in the blood compared to the control group. These results indicate that the PNA-peptide antisense antibiotic are efficacious in vivo.

All patents, patent applications and publications cited herein are fully incorporated by reference.

What is claimed is:

1. An antisense molecule or salt thereof that inhibits the growth of *Staphylococcus aureus* comprising a polynucleotide sequence that is antisense to the coding region of a *Staphylococcus aureus* membrane stability protein and hybridizes to said coding region under physiological conditions, wherein said antisense molecule has a sequence selected from the group consisting of SEQ ID NOs: 1-9 and 11-16, and wherein said antisense molecule is conjugated to a cell penetration molecule.

2. The antisense molecule of claim 1, that comprises a nucleotide sequence at least 80% identical to a sequence selected from the group consisting of SEQ ID NOs: 1-9 and 11-16.

3. The antisense molecule of claim 1, that comprises a nucleotide sequence selected from the group consisting of SEQ ID NOs: 1-9 and 11-16.

4. The antisense molecule of claim 1 which is an oligonucleotide.

5. The antisense molecule of claim 1, which is substantially pure.

6. The antisense molecule of claim 1, wherein the antisense molecule comprises a modified backbone.

7. The antisense molecule of claim 6, wherein the modified backbone is a PNA backbone.

8. The antisense molecule of claim 1, wherein said cell penetration molecule is a peptide.

9. A composition comprising an antisense molecule of claim 8, complexed to a delivery polymer.

10. The composition of claim 9, wherein said delivery polymer is a cationic block copolymer comprising phosphonium or ammonium ionic groups.

11. A method of inhibiting the growth of *Staphylococcus aureus*, comprising administering an antisense molecule of claim 1 to a tissue containing said *Staphylococcus aureus* or suspected of containing *Staphylococcus aureus*.

12. The method of claim 11, comprising topical administration of the antisense molecule.

13. A method of treating *Staphylococcus aureus* infection, comprising administering to an animal in need thereof an effective amount of the antisense molecule of claim 1.

14. The method of claim 11, wherein said antisense molecule is complexed to a delivery polymer.

15. The method of claim 13, wherein said antisense molecule is complexed to a delivery polymer.

16. The antisense molecule of claim 1, wherein the antisense molecule inhibits expression of multimodular transpeptidase transglycosylase/Penicillin-binding protein IA/B (PBP1) or UDP-N-acetylglucosamine 1-carboxyvinyl-transferase.

* * * * *